(12) United States Patent
Chava et al.

(10) Patent No.: US 11,299,477 B2
(45) Date of Patent: Apr. 12, 2022

(54) PROCESS FOR THE PREPARATION OF PAZOPANIB OR A PHARMACEUTICALLY ACCEPTABLE SALT THEREOF

(71) Applicant: Laurus Labs Limited, Hyderabad (IN)

(72) Inventors: Satyanarayana Chava, Hyderabad (IN); Seeta Rama Anjaneyulu Gorantla, Hyderabad (IN); Venkata Sunil Kumar Indukuri, Hyderabad (IN); Sanjay Kumar Dehury, Hyderabad (IN); Nagaraju Mekala, Hyderabad (IN); Jahangeer Baba Shaik, Hyderabad (IN); Durga Prasad Kuchipudi, Hyderabad (IN)

(73) Assignee: Laurus Labs Limited, Andhra Pradesh (IN)

( * ) Notice: Subject to any disclaimer, the term of this patent is extended or adjusted under 35 U.S.C. 154(b) by 7 days.

(21) Appl. No.: 16/802,273

(22) Filed: Feb. 26, 2020

(65) Prior Publication Data

US 2020/0262821 A1 Aug. 20, 2020

Related U.S. Application Data

(62) Division of application No. 15/034,797, filed as application No. PCT/IN2014/000712 on Nov. 5, 2014, now Pat. No. 10,730,859.

(30) Foreign Application Priority Data

Nov. 5, 2013 (IN) .......................... 4981/CHE/2013
Dec. 4, 2013 (IN) .......................... 5591/CHE/2013

(51) Int. Cl.
*C07D 403/12* (2006.01)

(52) U.S. Cl.
CPC .................................. *C07D 403/12* (2013.01)

(58) Field of Classification Search
CPC .................................................. C07D 403/12
See application file for complete search history.

(56) References Cited

U.S. PATENT DOCUMENTS

| 7,105,530 | B2* | 9/2006 | Boloor ................ A61P 7/00 514/275 |
| 7,262,203 | B2 | 8/2007 | Boloor et al. |
| 8,114,885 | B2 | 2/2012 | Boloor et al. |
| 8,349,861 | B2 | 1/2013 | Hopf |
| 2006/0252943 | A1 | 11/2006 | Boloor et al. |
| 2008/0293691 | A1 | 11/2008 | Brigandi et al. |
| 2009/0005406 | A1 | 1/2009 | Pandite et al. |
| 2012/0197019 | A1 | 8/2012 | Bhanushali et al. |
| 2013/0245262 | A1 | 9/2013 | Reddy et al. |
| 2015/0225374 | A1 | 8/2015 | Johansson et al. |

FOREIGN PATENT DOCUMENTS

| CN | 103373989 A | 10/2013 |
| WO | WO-02059110 A1 | 8/2002 |
| WO | WO-03106416 A2 | 12/2003 |
| WO | WO-2005/105094 A2 | 11/2005 |
| WO | WO-2006/020564 A1 | 2/2006 |
| WO | WO-2007/064753 A2 | 6/2007 |
| WO | WO-2007/143483 A2 | 12/2007 |
| WO | WO-2011/050159 A1 | 4/2011 |
| WO | WO-2011/058179 A1 | 5/2011 |
| WO | WO-2011/069053 A1 | 6/2011 |
| WO | WO-2012/073254 A1 | 6/2012 |
| WO | WO-2014/097152 A1 | 6/2014 |

OTHER PUBLICATIONS

J.H. Poupaert, Drug Design: Basic Principles and Applications, in 2 Encyclopedia of Pharmaceutical Technology 1362-1369, 1367 (James Swarbrick ed., 3rd ed., 2007).
Qi, Haofei, et al. "Synthesis of Pazopanib Hydrochloride [J]." Chinese Journal of Modern Applied Pharmacy 1 (2011): 017.
Wang, Yong-zhen, Yan-jin Zhao, and Shu-xin Li. "Synthesis of Pazopanib Hydrochloride." Fine Chemical Intermediates 2 (2013): 012, pp. 46-48.
R. Wilson et al., 71 Journal of Organic Chemistry 8329-8351, 8326 (2006).
N.G. Anderson, Practical Process & Research Development 27-52 (2000).
Y. Mei et al., 9 Letters in Organic Chemistry. 276-279 (2012).
N.G. Anderson, Practical Process & Research Development 53-111, (2000).
Yang, Zhi-hui, et al. "Improved Synthesis of Pazopanib Hydrochloride [J]." Fine Chemical Intermediates 4 (2011): 013.
P.A. Harris et al., 51 Journal of Medicinal Chemistry, 4632-4640 (2008).
Yan, C. H. E. N., and F. A. N. G. Zheng. "2, We Ping1 (1. College ot Biotechnology and Pharmaceutical Engineering, Nanjing University of Technology; 2. School of Pharmaceutical Science, Nanjing University of Technology, Nanjing 210009); Synthesis of Pazopanib Hydrochloride [J]." Chinese Journal of Pharmaceuticals 5 (2010). pp. 326-328.
Qian, Hai. A Novel Practical Synthesis of Pazopanib: An Anticancer Drug, Letters in Organic Chemistry 9(4) 276-279 (2012).
O. Ottoni et al., 54 Tetrahedron 13915-13928 (1998).

\* cited by examiner

*Primary Examiner* — Bruck Kifle
(74) *Attorney, Agent, or Firm* — Blank Rome LLP

(57) ABSTRACT

The present invention is relates to an improved process for the preparation of pazopanib or a pharmaceutically acceptable salts thereof. The present invention also relates to novel polymorphic Forms of pazopanib hydrochloride, and its intermediates thereof.

14 Claims, 26 Drawing Sheets

PROCESS FOR THE PREPARATION OF PAZOPANIB OR A PHARMACEUTICALLY ACCEPTABLE SALT THEREOF

CROSS-REFERENCE TO RELATED APPLICATIONS

This is a divisional application that is based on and claims the benefit of the filing date and disclosure of U.S. patent application Ser. No. 15/034,797, filed on May 5, 2016, entitled "An Improved Process for the Preparation of Pazopanib or a Pharmaceutically Acceptable Salt Thereof," which is a national phase of PCT/IN2014/000712, filed on Nov. 5, 2014, which claims the benefit of Indian Provisional Application No. 4981/CHE/2013 filed on Nov. 5, 2013, entitled "An improved process for the preparation of Pazopanib or a pharmaceutically acceptable salt thereof," and 5591/CHE/2013 filed on Dec. 4, 2013, entitled "Novel polymorphs of pazopanib hydrochloride and intermediates thereof," the content of each of which are incorporated by reference herein.

FIELD OF THE INVENTION

The present invention generally relates to an improved process for the preparation of Pazopanib or a pharmaceutically acceptable salt thereof.

The present invention also relates to novel polymorphic Forms of Pazopanib hydrochloride, processes for its preparation and pharmaceutical compositions containing the same.

The present invention also relates to novel polymorphic Forms of intermediates of pazopanib hydrochloride and processes for its preparation.

BACKGROUND OF THE INVENTION

Pazopanib is a tyrosine kinase indicator, belonging to a class of substituted pyrimidine derivative. It is designated chemically as 5-[[4-[(2,3-dimethyl-2H-indazol-6-yl)methylamino]-2-pyrimidinyl]amino]-2-methyl benzenesulfonamide, is represented by the following structure of Formula I:

Formula I

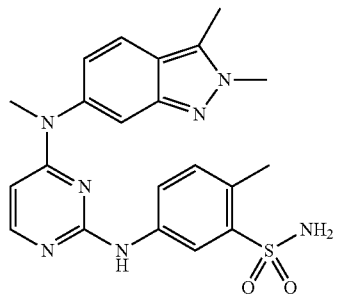

Pazopanib is marketed as hydrochloride salt by Glaxosmithkline under the trade name VOTRIENT® is tyrosine kinase inhibitor and indicated for the treatment of patients with advanced renal cell carcinoma (RCC) and treatment of patients with advanced soft tissue sarcoma (STS) who have received prior chemotherapy.

U.S. Pat. No.(s). U.S. Pat. No. 7,105,530 ("the '530 patent"), U.S. Pat. No. 7,262,203 ("the '203 patent") and U.S. Pat. No. 8,114,885 ("the '885 patent") discloses a variety of pyrimidineamines and their derivatives such as Pazopanib, processes for their preparation, pharmaceutical compositions comprising the derivatives, and method of use thereof.

The process disclosed in the '530 patent is schematically represented as follows:

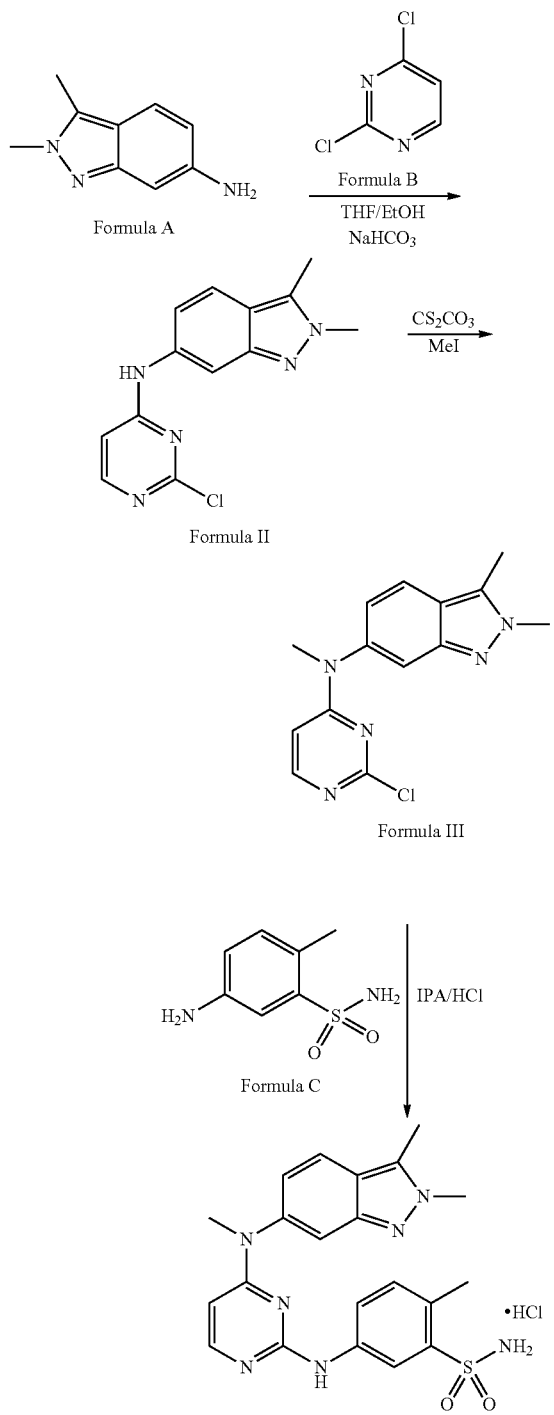

Patent publication No. WO 2011/050159 ("the '159 publication") disclosed process for preparation of Pazopanib hydrochloride, which involves condensation of 2,3-dimethyl-2H-indazol-6-amine of Formula A and 2,4-dichloropyrimidine of Formula B in a solvent like industrial methylated sprit and specific reaction conditions like, in presence of a base, sodium bicarbonate having a particle size distribution of >250 μm or 50 to 150 μm selected to ensure that the pH of the reaction mixture is less than 7 for the reaction time period not more than 300 min to obtain N-(2-chloro-pyrimidin-4-yl)-2,3-dimethyl-2H-indazol-6-amine of Formula II. The compound of Formula II was methylated in presence of a methylating agent in an organic solvent like dimethylformamide by using specific reaction conditions like, in presence of a base i.e. Potassium carbonate having a particle size distribution D99 of >300 μm or D99 of <200 μm selected to ensure that the reaction time needs to reduce the starting material to less than 2% in less than 8 hrs to obtain N-(2-chloropyrimidin-4-yl)-N-2,3-trimethyl-2H-indazol-6-amine of Formula III. The resultant methylated compound was condensed with 5-amino-2-methylbenzenesulfonamide of Formula C in presence of 4M HCl and methanol to yield Pazopanib hydrochloride.

WO '159 publication disclosed that use of sodium bicarbonate with specific particle size distribution of >250 μm or 50 to 150 μm is key element in condensation of compound of Formula A and Formula B to minimize the formation of Impurity of Formula 1 within the range of about 0.05-4.0%.

Impurity 1

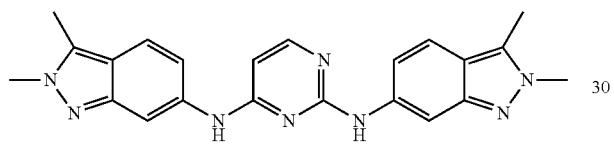

WO '159 publication also disclosed that use of potassium carbonate with specific particle size distribution D99 of >300 μm or D99 of <200 μm is key element in methylation of compound of Formula II to reduce the formation of Impurities of Formula 2, Formula 3 and Formula 4 within the range of about 0.05-3%.

Impurity 2

Impurity 3

Impurity 4

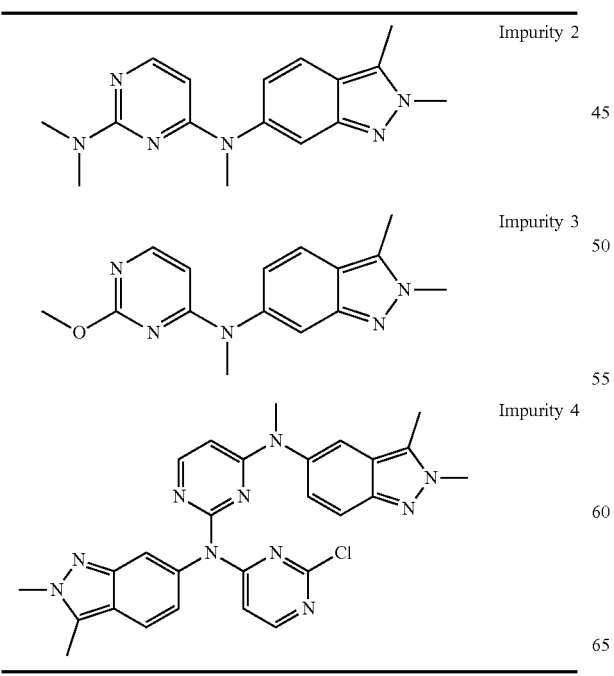

Patent publication No. WO 2012/073254 ("the '254 publication") disclosed a process for preparation of pazopanib hydrochloride, which involves condensation of 2,4-dichloropyrimidine of Formula B with 5-amino-2-methylbenzenesulfonamide of Formula C in presence of a base like sodium bicarbonate and a solvent like ethanol to yield 5-(4-chloropyrimidin-2-yl-amino)-2-methylbenzenesulfonamide. The resultant compound was condensed with N-2,3-trimethyl-2H-indazole-6-amine of Formula D in an alcoholic solvent like ethanol. WO '254 publication also discloses process for purification of pazopanib hydrochloride from alcoholic solvent and water. The process disclosed in the '254 publication is schematically represented as follows:

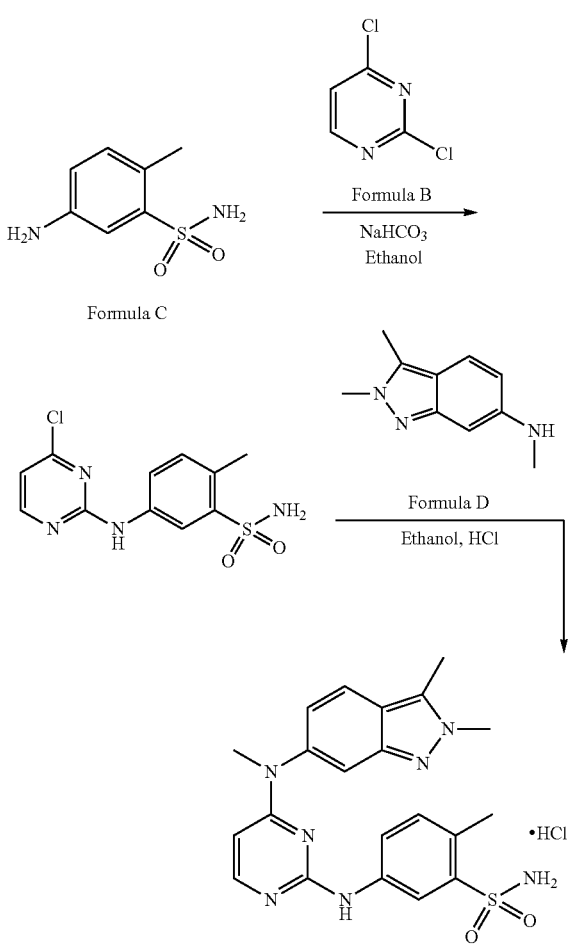

Patent publication No. IN 2505/CHE/2011 disclosed a process for preparation of pazopanib, which involves condensation of 2,3-dimethyl-2H-indazol-6-amine of Formula A and 2,4-dichloropyrimidine of Formula B in presence of sodium bicarbonate and a phase transfer catalyst like tetrabutyl ammonium bromide in a solvent like methanol to obtain N-(2-chloropyrimidin-4-yl)-2,3-dimethyl-2H-indazol-6-amine of Formula II. The resultant compound was methylated in presence of methyl iodide, potassium carbonate in a solvent like dimethylformamide to obtain compound of Formula III. The obtained Formula III was condensed with 5-amino-2-methylbenzenesulfonamide of Formula C in presence of dimethylformamide and concentrated HCl to yield pazopanib hydrochloride.

Patent publication No. CN 103373989 ("the '989 publication") disclosed a process for preparation of Pazopanib intermediate of Formula III by condensation of N-2,3-trimethyl-2H-indazole-6-amine of Formula D with 2,4-dichloropyrimidine of Formula B in presence of sodium bicarbonate and THF.

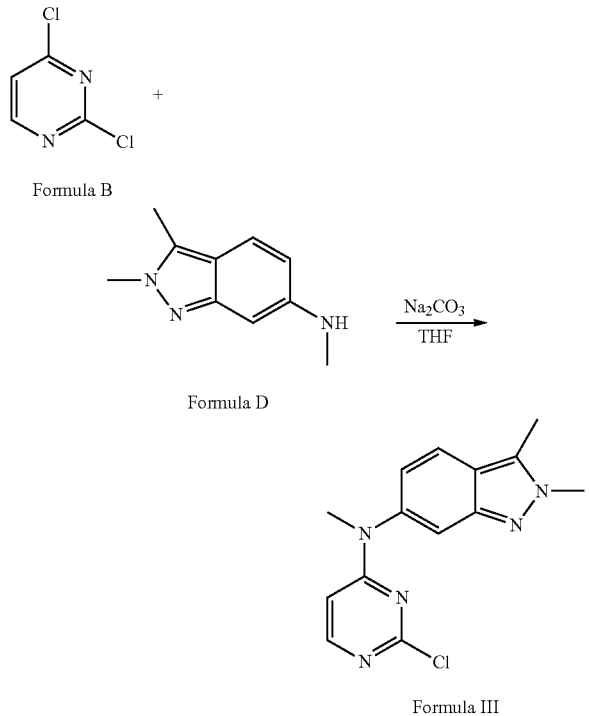

Formula B

Formula D

Formula III

Patent publication No. WO 2014/97152 ("the '152 publication") disclosed a process for preparation of Pazopanib hydrochloride starting from 2,3-dimethyl-6-nitro-2H-indazole.

The processes for preparation of pazopanib described in the above literature have certain drawbacks as it involves: a) use of specific predefined particles of bases like sodium bicarbonate and potassium carbonate, which involves additional process steps like milling, grinding etc, b) use of expensive phase transfer catalysts and c) multiple steps making the process quite expensive, particularly on large scale.

European Medicines Agency (EMA) public assessment report disclosed that pazopanib hydrochloride is a white to slightly yellow, non-hygroscopic, crystalline substance and the manufacturing process consistently produces pazopanib hydrochloride Form 1. However, the EMEA does not describe any particular characterization data for the disclosed polymorph Form 1.

PCT Publication No. WO 2011/058179 ("the '179 publication") discloses pazopanib base crystalline Forms such as Form-I and Form-II and a process for its preparation; also disclosed characterization data of Form-I and Form-II by XRD, IR and melting point.

PCT Publication No. WO 2011/069053 ("the '053 publication") discloses crystalline pazopanib base and crystalline pazopanib hydrochloride Forms such as Form-II, Form-III, Form-IV, Form-V, Form-VI, Form-VIII, Form-IX, Form-X, Form-XI, Form-XII, Form-XIII, Form-A, Form-G and also discloses crystalline Pazopanib dihydrochloride Forms such as Form-I, Form-XIV, Form-XV. The crystalline Forms reported in the PCT publication characterized by its XRD pattern.

IN Publication No. 3023/CHE/2010 discloses crystalline pazopanib dihydrochloride Form-I and crystalline pazopanib mono hydrochloride, process for it preparation and characterization by XRD of the same.

IN Publication No. 1535/CHE/2012 discloses crystalline pazopanib hydrochloride Form-SP and a process for its preparation; also disclosed characterization data of Form-SP by XRD, DSC and IR.

PCT Publication No(s): WO 2007/143483, WO 2007/064753, WO 2006/20564 and WO 2005/105094 as well as US Publication No. US 2008/0293691 disclose anhydrous and hydrated Forms of pazopanib hydrochloride and their process for preparation thereof.

IP.Com journal disclosure Number IPCOM000207426D discloses crystalline Form of pazopanib hydrochloride Form-R, which is characterized by XRD pattern.

Further, IP.Com journal disclosure Number IPCOM000193076D discloses crystalline Forms of N-(2-chloropyrimidin-4-yl)-N-2,3-trimethyl-2H-indazol-6-amine of Formula III such as Form I and Form II along with characteristic data of XRD pattern.

Polymorphism is the occurrence of different crystalline forms of a single compound and it is a property of some compounds and complexes. Thus, polymorphs are distinct solids sharing the same molecular formula, yet each polymorph may have distinct physical properties. Therefore, a single compound may give rise to a variety of polymorphic forms where each form has different and distinct physical properties, such as different solubility profiles, different melting point temperatures and/or different x-ray diffraction peaks. Since the solubility of each polymorph may vary, identifying the existence of pharmaceutical polymorphs is essential for providing pharmaceuticals with predicable solubility profiles. It is desirable to investigate all solid state forms of a drug, including all polymorphic forms and solvates, and to determine the stability, dissolution and flow properties of each polymorphic form. Polymorphic forms and solvates of a compound can be distinguished in a laboratory by X-ray diffraction spectroscopy and by other methods such as, infrared spectrometry. Additionally, polymorphic forms and solvates of the same drug substance or active pharmaceutical ingredient, can be administered by itself or formulated as a drug product (also known as the final or finished dosage form), and are well known in the pharmaceutical art to affect, for example, the solubility, stability, flowability, tractability and compressibility of drug substances and the safety and efficacy of drug products.

The discovery of new polymorphic forms and solvates of a pharmaceutically useful compound, like pazopanib, may provide a new opportunity to improve the performance characteristics of a pharmaceutical product. It also adds to the material that a formulation scientist has available for designing, for example, a pharmaceutical dosage form of a drug with a targeted release profile or other desired characteristic.

Hence there remains a need for an improved process to prepare pazopanib or a pharmaceutically acceptable salt thereof and novel polymorphs of pazopanib or a pharmaceutically acceptable salt thereof, particularly pazopanib hydrochloride, which is cost effective, industrially viable, and provide pazopanib substantially free of aforementioned impurities.

The present invention provides an improved process for the preparation of pazopanib or a pharmaceutically acceptable salt thereof, with improved purity and low levels of process impurities including genotoxic impurities as compared to the prior-art processes without restricting to base specific particle size.

The present invention also provides new polymorphic forms of the pazopanib hydrochloride, which are designated as pazopanib hydrochloride Form-L1, Form-L2, Form-L3, Form-L4, Form-L5, Form-L6, Form-L7, Form-L8 and Form-L9.

The present invention further provides novel polymorphic Forms of N-(2-chloropyrimidin-4-yl)-N-2,3-trimethyl-2H-indazol-6-amine (Formula III), which is an key intermediate in the preparation of pazopanib. The new crystalline polymorphic Forms of Formula III have been designated as Form-K1, Form-K2, Form-K3 and Form-K4.

SUMMARY OF THE INVENTION

The present invention provides an improved process for the preparation of pazopanib or a pharmaceutically acceptable salt thereof without limiting to the any specific particle size of base.

The present invention also provides novel polymorphic Forms of pazopanib hydrochloride, processes for its preparation and pharmaceutical compositions comprising one or more of the novel polymorphic Forms of pazopanib hydrochloride.

The present invention also provides novel polymorphic Forms of N-(2-chloropyrimidin-4-yl)-N-2,3-trimethyl-2H-indazol-6-amine (Formula III), an intermediate of pazopanib hydrochloride, and processes for its preparation.

The present invention further provides processes for preparation of pazopanib hydrochloride Form 1.

In accordance with one embodiment, the present invention provides an improved process for preparation of pazopanib or a pharmaceutically acceptable salt thereof of Formula I, Formula I

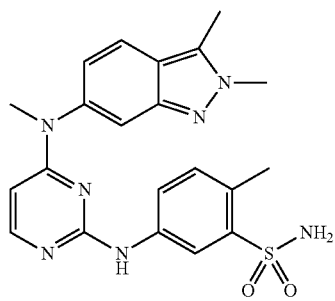

comprising:
a) reacting a compound of Formula A with a compound of Formula B in a solvent (S1) in presence of a base (B1) to obtain a compound of Formula II, Formula A

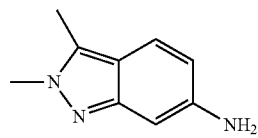

Formula B

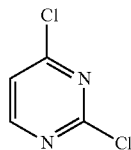

Formula II

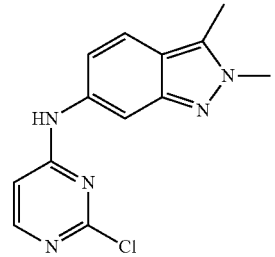

b) reacting the obtained compound of Formula II with a methylating agent in a solvent (S2) in presence of a base (B2) to obtain a compound of Formula III, and Formula III

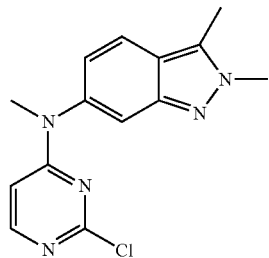

c) condensing the compound of Formula III with Formula C in a solvent (S3) to obtain pazopanib or a pharmaceutically acceptable salts thereof Formula C

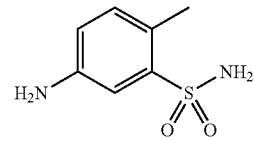

wherein the base (B1) is selected from inorganic or organic base except sodium bicarbonate and the base (B2) is selected form inorganic or organic base except potassium carbonate and cesium carbonate.

In accordance with a second embodiment, the present invention provides an improved process for preparation of pazopanib or a pharmaceutically acceptable salt thereof of Formula I, comprising:
a) reacting a compound of Formula A with a compound of Formula B in a solvent (S1) in presence of a base (B1) to obtain a compound of Formula II,
b) reacting the obtained compound of Formula II with a methylating agent in a solvent (S2) in presence of a base (B2) to obtain a compound of Formula III, and
c) condensing the compound of Formula III with Formula C in a solvent (S3) to obtain pazopanib or a pharmaceutically acceptable salts thereof; wherein the base (B1) and (B2) particles are not limited to any specific particle size.

In accordance with a third embodiment, the present invention provides an improved process for preparation of pazopanib or a pharmaceutically acceptable salt thereof of Formula I, comprising:
a) reacting a compound of Formula A with compound of Formula B in a solvent (S1) in presence of a base (B1) to obtain compound of Formula II, and
b) converting the compound of Formula II in to pazopanib or a pharmaceutically acceptable salt thereof; wherein the base (B1) is selected from inorganic or organic base except sodium bicarbonate.

In accordance with a fourth embodiment, the present invention provides an improved process for preparation of pazopanib or a pharmaceutically acceptable salt thereof of Formula I, comprising:
a) reacting a compound of Formula A with compound of Formula B in a solvent (S1) in presence of a base (B1) to obtain compound of Formula II, and
b) converting the compound of Formula II in to pazopanib or a pharmaceutically acceptable salt thereof;
wherein the base (B1) is selected from inorganic base such as ammonia, alkali or alkaline earth metal hydroxides, alkali or alkaline earth metal alkoxides, alkali or alkaline earth metal carbonates, alkali or alkaline earth metal bicarbonates and the like except sodium bicarbonate; or organic bases such as alkyl or aryl amine.

In accordance with a fifth embodiment, the present invention provides an improved process for preparation of pazopanib or a pharmaceutically acceptable salt thereof of Formula I, comprising:
a) reacting a compound of Formula II with a methylating agent in a solvent (S2) in presence of a base (B2) to obtain a compound of Formula III, and
b) converting the compound of Formula III in to pazopanib or a pharmaceutically acceptable salt thereof; wherein the base (B2) is selected from inorganic or organic base except potassium carbonate or cesium carbonate.

In accordance with a sixth embodiment, the present invention provides an improved process for preparation of pazopanib or a pharmaceutically acceptable salt thereof of Formula I, comprising:
a) reacting a compound of Formula II with a methylating agent in a solvent (S2) in presence of a base (B2) to obtain a compound of Formula III, and
b) converting the compound of Formula III in to pazopanib or a pharmaceutically acceptable salt thereof;
wherein the base (B2) is selected from inorganic base such as ammonia, alkali or alkaline earth metal hydroxides, alkali or alkaline earth metal alkoxides, alkali or alkaline earth metal carbonates, alkali or alkaline earth metal bicarbonates and the like except potassium carbonate or cesium carbonate; organic bases such as alkyl or aryl amine.

In accordance with a seventh embodiment, the present invention provides novel polymorphic Forms of pazopanib hydrochloride; wherein the polymorphic Forms have been designated as pazopanib hydrochloride Form-L1, pazopanib hydrochloride Form-L2, pazopanib hydrochloride Form-L3, pazopanib hydrochloride Form-L4, pazopanib hydrochloride Form-L5, pazopanib hydrochloride Form-L6, pazopanib hydrochloride Form-L7, pazopanib hydrochloride Form-L8 and pazopanib hydrochloride Form-L9.

In accordance with an eight embodiment, the present invention provides novel polymorphic Forms of N-(2-chloropyrimidin-4-yl)-N-2,3-trimethyl-2H-indazol-6-amine (Formula III); wherein the crystalline Forms are designated as Form-K1, Form-K2, Form-K3 and Form-K4.

In accordance with a ninth embodiment, the present invention provides a process for preparation of pazopanib hydrochloride Form 1, comprising:
a) providing a solution of pazopanib hydrochloride Form-L8 in methanol,
b) partial evaporation of the solvent from the resultant solution,
c) adding hydrochloric acid to the resultant reaction solution of step b); and
d) isolating the pazopanib hydrochloride Form 1; wherein the pazopanib hydrochloride Form-L8 characterized by an XRPD pattern substantially in accordance with FIG. 16.

In accordance with a tenth embodiment, the present invention provides a process preparation of pazopanib hydrochloride Form 1, comprising:
a) heating pazopanib hydrochloride Form-L8 up to a temperature of about 180° C.,
b) cooling to room temperature, and
c) recovering the pazopanib hydrochloride Form 1; wherein the pazopanib hydrochloride Form-L8 characterized by an XRPD pattern substantially in accordance with FIG. 16.

In accordance with an eleventh embodiment, the present invention provides a process for preparation of pazopanib hydrochloride Form 1, comprising:
a) condensation of compound of Formula III and Formula C in an alcohol solvent in presence of catalytic amount of hydrochloric acid,
b) cooling the solution to precipitation, and
c) isolating the pazopanib hydrochloride Form 1; where in the alcohol solvent is selected from the group consisting of n-propanol, n-butanol and 2-butanol.

In accordance with a twelfth embodiment, the present invention provides a pharmaceutical composition comprising pazopanib or a pharmaceutically acceptable salt and its polymorphic forms thereof, particularly pazopanib hydrochloride prepared by the processes of the present invention and at least one pharmaceutically acceptable excipient.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE INVENTION

Figure 1:
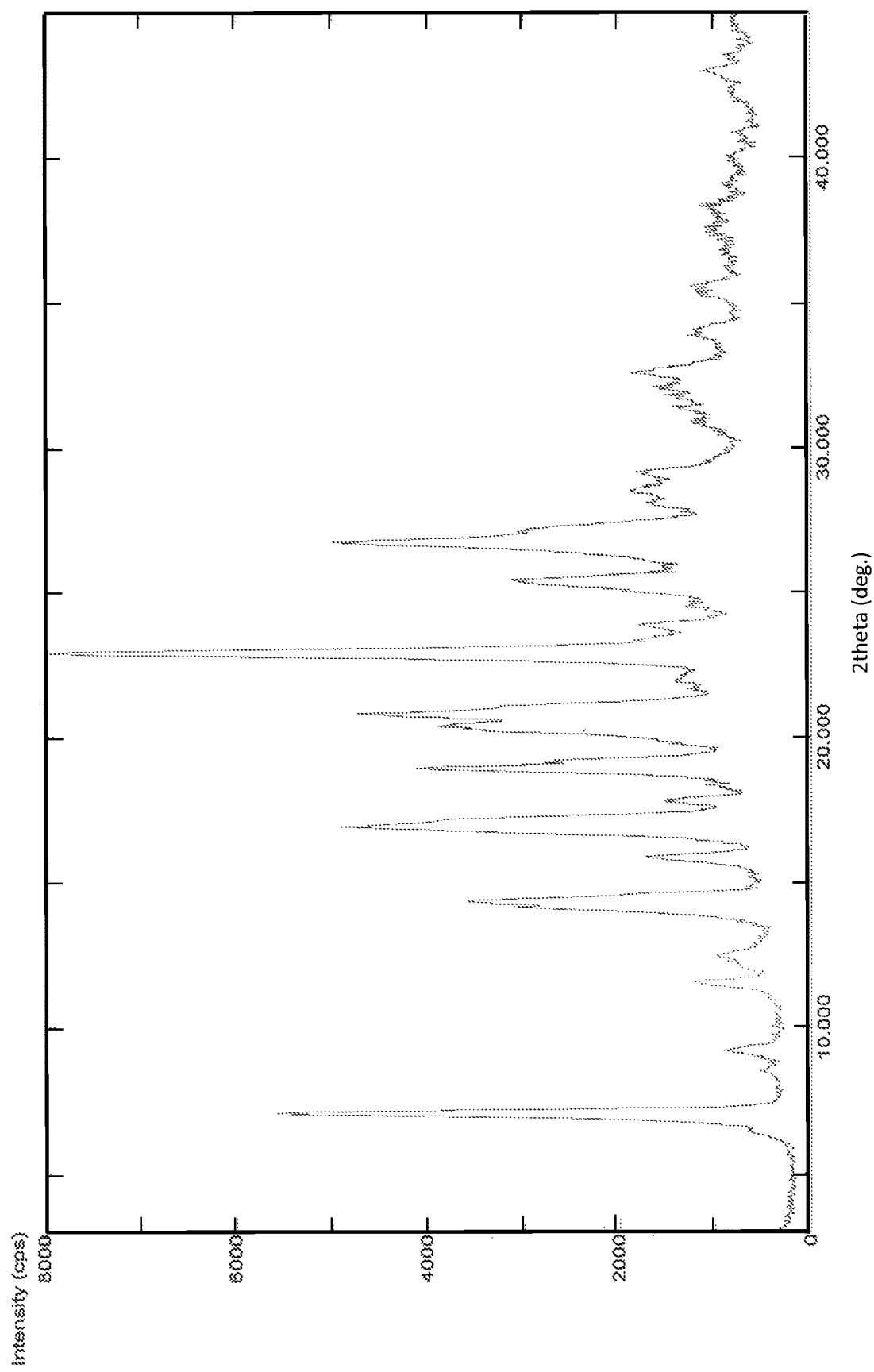
FIG. 1 is the characteristic powder X-ray diffraction (XRD) pattern of Pazopanib hydrochloride Form-L1.

The present invention encompasses an improved process for preparation of pazopanib or a pharmaceutically acceptable salt thereof.

The present invention also provides novel polymorphic Forms of pazopanib hydrochloride, processes for preparation thereof, and pharmaceutical compositions comprising one or more of such polymorphic Forms.

The present invention also provides novel polymorphic Forms of Formula III, an intermediate of pazopanib hydrochloride, and processes for its preparation.

The present invention further provides processes for preparation of pazopanib hydrochloride Form 1.

In one embodiment, the present invention provides an improved process for preparation of pazopanib or a pharmaceutically acceptable salt thereof of Formula I,

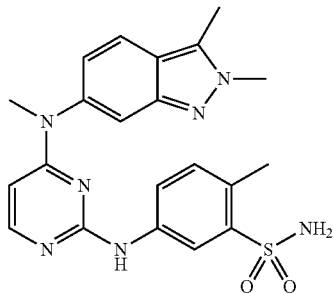

Formula I comprising:
a) reacting a compound of Formula A with a compound of Formula B in a solvent (S1) in presence of a base (B1) to obtain a compound of Formula II,

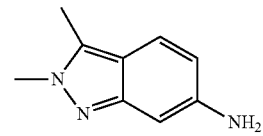

Formula A

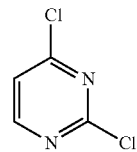

Formula B

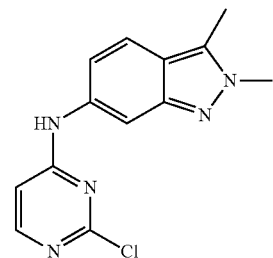

Formula II b) reacting the obtained compound of Formula II with a methylating agent in a solvent (S2) in presence of a base (B2) to obtain a compound of Formula III, and

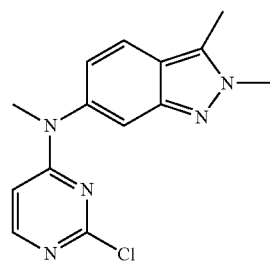

Formula III c) condensing the compound of Formula III with Formula C in a solvent (S3) to obtain pazopanib or a pharmaceutically acceptable salts thereof

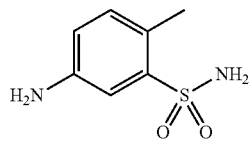

Formula C wherein the base (B1) is selected from inorganic or organic base except sodium bicarbonate and the base (B2) is selected from inorganic or organic base except potassium carbonate or cesium carbonate.

The compound of Formula A and Formula C can be prepared by using an adaptation of literature methods, such as described in US 2006/252943 and US 2008/293691.

The reported literatures disclose a process for preparation of pazopanib hydrochloride, which involves use of bases with specific particle size to limit the impurities. The present invention describes an improved process for preparation of pazopanib hydrochloride, which involves bases, where such bases are not limited to any specific particle size, yielding lower levels of impurities and high pure final product as compared to the prior-art processes.

In another embodiment of the present invention, the base (B1) includes inorganic base such as ammonia, alkali or alkaline earth metal hydroxides, alkali or alkaline earth metal alkoxides, alkali or alkaline earth metal carbonates, alkali or alkaline earth metal bicarbonates and the like except sodium bicarbonate. Preferably sodium hydroxide, potassium hydroxide, lithium hydroxide, cesium hydroxide, calcium hydroxide, magnesium hydroxide, barium hydroxide, sodium methoxide, sodium ethoxide, sodium tertiary butoxide, potassium tertiary butoxide, magnesium tertiary butoxide, sodium carbonate, potassium carbonate, lithium carbonate, cesium carbonate, magnesium carbonate, potassium bicarbonate, magnesium bicarbonate and the like and mixtures thereof; more preferably sodium hydroxide, sodium carbonate, potassium carbonate, potassium bicarbonate and mixtures thereof.

In another embodiment, the base (B1) used herein is an inorganic base and is not limited to any specific particle size.

In another embodiment of the present invention, the base (B1) includes organic bases such as alkyl or aryl amine. Preferably triethylamine, pyridine, N-methyl morpholine, diisopropylethylamine, imidazole, dimethylaminopyridine, 1,4-diazabicyclo[2.2.2] octane (DABCO), 1,8-Diazabicyclo [5.4.0]undec-7-ene (DBU), N,N-dimethylaniline, N,N-diethylaniline, and mixtures thereof; more preferably the base (B1) is selected from triethyl amine, N-methyl morpholine, diisopropylethylamine and mixtures thereof; most preferably triethylamine.

The solvent (S1) includes, but is not limited to aromatic hydrocarbons, ethers, amides, nitriles and the like, water and mixtures thereof. The aromatic hydrocarbons such as toluene, xylene, chlorobenzene and the like and mixtures thereof; ethers such as dimethyl ether, diethyl ether, methyl ethyl ether, diisopropyl ether, methyl tertiary butyl ether, tetrahydrofuran, 1,4-dioxane and the like and mixtures thereof; amides such as dimethyl formamide, dimethylsulfoxide, dimethyl acetamide, N-methyl pyrrolidinone and the like and mixtures thereof; nitriles such as acetonitrile, propionitrile and mixtures thereof; preferably the solvent (S1) is dimethyl formamide, water or mixtures thereof.

The reaction of compound of Formula A and Formula B is carried out at a temperature of about 25° C. to 90° C.; preferably at about 25° C. to about 50° C.

After completion of the reaction, the reaction mass may be treated with a suitable aqueous acid such as hydrochloric acid, acetic acid and the like and then filtered the precipitated solids by methods known in the art, for example filtration and the resultant product may optionally be further dried.

Then, the obtained solid compound may be optionally purified by dissolving it in an organic solvent followed by refluxing the reaction mass for a period of about 1 hour to about 8 hours and isolating the compound of Formula II by methods known in the art, for example cooling the solution to less than 30° and then filtration to get pure compound.

The organic solvent includes, but is not limited to ethers include, but are not limited to methyl ethyl ether, methyl tertiary butyl ether, tetrahydrofuran, 1,4-dioxane and the like and mixtures thereof; nitriles include, but are not limited to acetonitrile, propionitrile and the like; water and mixtures thereof preferably the organic solvent is acetonitrile.

The resultant product may optionally be further dried. Drying can be suitably carried out in a tray dryer, vacuum oven, air oven and the like. The drying can be carried out at a temperature ranging from about 40° C. to about 90° C. A high purity level of the resulting Formula II, obtained by the aforementioned process, may have a chemical purity of at least about 95%, as measured by HPLC, preferably at least about 98%, as measured by HPLC and more preferably at least about 99%, as measured by HPLC; and contains less than 0.1% of dimer impurity of Formula 1, as measured by HPLC, preferably less than 0.05%, as measured by HPLC; and less than 0.5% of Impurity 5 as measured by HPLC, preferably less than 0.2% as measured by HPLC.

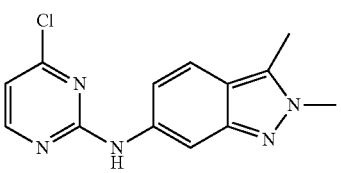

Impurity 5

In another embodiment, the present invention provides an improved process for the preparation of pazopanib or pharmaceutically acceptable salts thereof, comprising providing a compound of Formula II as obtained by the process described above, as a starting material or as an intermediate. The yield and the purity of the pazopanib hydrochloride prepared from compound of Formula may have purity equal to or greater than about 99.5% as measured by HPLC.

The step b) of the aforementioned process involves reaction of the compound of Formula II, obtained by the process described step a) as above with a methylating agent, in a solvent (S2) and base (B2) to obtain a compound of Formula III.

The methylating agent may be used in the process of step b) is selected from the group consisting of methyl iodide, methyl bromide, methyl chloride, dimethylsulfate, methyl nitrate, methyl mesylate, methyl besylate, methyl tosylate, 2,2,2-trichloroacetimidate, trimethyloxonium tetrafluoroborate, Trimethyl sulfoxonium iodide, Trimethylsulfoxonium bromide, Trimethylsulfoxonium chloride and methyl triflate and the like; preferably the methylating agent is methyl iodide or dimethylsulfate.

The solvent (S2) includes alcohols, ethers, amides, ketones, nitriles, water and mixtures thereof. Preferably, alcohols such as methanol, ethanol, isopropanol and the like; ethers such as tetrahydrofuran, methyl tertiary butyl ether, diethyl ether and the like; amides such as dimethyl formamide, dimethylsulfoxide, dimethyl acetamide and the like; ketones such as acetone, methyl isobutyl ketone, methyl ethyl ketone and the like; nitrites such as acetonitrile, propionitrile and the like; water and mixtures thereof; more preferably methanol, acetone, dimethyl formamide; most preferably acetone.

The base (B2) includes inorganic base such as ammonia, alkali or alkaline earth metal hydroxides, alkali or alkaline earth metal alkoxides, alkali or alkaline earth metal carbonates, alkali or alkaline earth metal bicarbonates and the like except potassium carbonate or cesium carbonate. Preferably sodium hydroxide, potassium hydroxide, lithium hydroxide, cesium hydroxide, calcium hydroxide, magnesium hydroxide, barium hydroxide, sodium methoxide, sodium ethoxide, sodium tertiary butoxide, potassium tertiary butoxide, magnesium tertiary butoxide, sodium carbonate, lithium carbonate, magnesium carbonate, sodium bicarbonate, potassium bicarbonate, magnesium bicarbonate and the like and mixtures thereof; more preferably sodium hydroxide, sodium carbonate, sodium bicarbonate, potassium bicarbonate and mixtures thereof; most preferably sodium hydroxide.

In another embodiment, the base (B2) used herein is an inorganic base and is not limited to any specific particle size.

In another embodiment of the present invention, the base (B2) includes organic bases such as alkyl or aryl amine. Preferably triethylamine, pyridine, N-methyl morpholine, diisopropylethylamine, imidazole, dimethylaminopyridine, 1,4-diazabicyclo[2.2.2] octane (DABCO), 1,8-Diazabicyclo[5.4.0]undec-7-ene (DBU), N,N-dimethylaniline, N,N-diethylaniline, and mixtures thereof; more preferably the base (B2) is selected from triethyl amine, N-methyl morpholine, diisopropylethylamine and mixtures thereof.

The reaction of compound of Formula II is carried out at a temperature of about 25° C. to about 60° C.; preferably at about 25° C. to about 50° C.

After completion of the reaction, the reaction mass may be neutralized with a suitable aqueous acid such as hydrochloric acid, acetic acid and the like and then concentrated reaction mass completely under vacuum. To the obtained residue water may be added and stirred for about 2 hours and the resultant compound of Formula III may be isolated by techniques known in the art, for example, filtration and the resultant product may optionally be further dried.

In another embodiment, the compound of Formula III thus obtained may be optionally purified by dissolving the compound of Formula III in a suitable solvent. The solvent may be heated to obtain a solution at a temperature of from about ambient temperature to about reflux temperature. The reaction solution may be cooled at a temperature from about 20° C. or less such that the compound of Formula III can be isolated by conventional techniques.

The suitable solvent may be selected from the group comprising esters such as methyl acetate, ethyl acetate, isopropyl acetate, butyl acetate and the like; nitriles such as acetonitrile, propionitrile and the like; ketones such as acetone, methyl ethyl ketone, methyl isobutyl ketone and the like; and mixtures thereof; preferably the suitable solvent is ethyl acetate.

The wet product may optionally be further dried. Drying can be suitably carried out in a tray dryer, vacuum oven, air oven and the like. The drying can be carried out at a temperature ranging from about 40° C. to about 90° C. A high purity level of the resulting Formula III, obtained by the aforementioned process, may have a chemical purity of at least about 95%, as measured by HPLC, preferably at least about 98%, as measured by HPLC and more preferably at least about 99%, as measured by HPLC and contains less than 0.1% of each of impurities i.e. Impurity 2, Impurity 3 and Impurity 4, as measured by HPLC, preferably less than 0.05%, as measured by HPLC; and less than 0.5% of Impurity 6 as measured by HPLC, preferably less than 0.2% as measured by HPLC.

Impurity 6

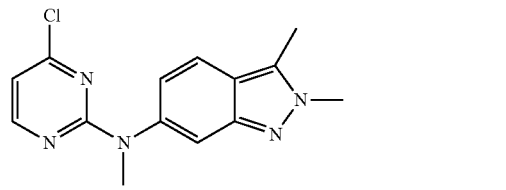

In another embodiment, the present invention provides an improved process for the preparation of pazopanib or pharmaceutically acceptable salts thereof, preferably pazopanib hydrochloride, comprising providing a compound of Formula III as obtained by the process described above, as a starting material or as an intermediate. The yield and purity of the pazopanib hydrochloride prepared from compound of Formula III may have purity equal to or greater than about 99.5% as measured by HPLC.

The step c) of the aforementioned process involves condensation of the compound of Formula III and Formula C optionally in presence of an acid in a solvent (S3) to obtain pazopanib or a pharmaceutically acceptable salt thereof.

The solvent (S3) includes alcohols, ethers, amides, ketones, nitriles and mixtures thereof. Preferably, alcohols such as methanol, ethanol, isopropanol and the like; ethers such as tetrahydrofuran, methyl tertiary butyl ether, diethyl ether and the like; amides such as dimethyl formamide, dimethylsulfoxide, dimethyl acetamide and the like; ketones such as acetone, methyl isobutyl ketone, methyl ethyl ketone and the like; nitriles such as acetonitrile, propionitrile and the like; water and mixtures thereof preferably methanol, tetrahydrofuran, acetonitrile or mixtures thereof.

The acid used herein selected from the group consisting of inorganic acids such as hydrochloric acid, hydrobromic acid, sulfuric acid, phosphoric acid and the like. The source of acid may be in the form of an aqueous, anhydrous or gas form, for example aqueous hydrochloric acid or solvent containing hydrochloric acid or hydrochloric acid gas, preferably a solvent containing hydrochloric acid can be used.

The solvent may be used for dissolving acid source is selected from the group consisting of methanol, ethanol, isopropanol and the like and mixtures thereof.

The condensation of compound of Formula III and Formula C is carried out at a temperature of about 25° C. to about reflux temperature; preferably at about 60° C. to about 65° C.

After completion of the reaction, the reaction mass may be cooled at a temperature from about 10° C. or less such that and the pazopanib hydrochloride can be isolated by conventional techniques known in the art, for example, filtration and the resultant product may optionally be further dried.

In another embodiment, the present invention provides a process for purification of pazopanib hydrochloride, comprising:
a) providing a solution of pazopanib hydrochloride in one or more organic solvents,
b) adding an acid or pazopanib hydrochloride seed to the step a) reaction mass, and
c) isolating the pazopanib hydrochloride.

The one or more organic solvents of step a) include, but are not limited to alcohols, esters, nitriles, halogenated solvents, aromatic hydrocarbons and mixtures thereof. Preferably, alcohols such as methanol, ethanol, isopropanol and the like; esters such as methyl acetate, ethyl acetate, isopropyl acetate and the like; nitriles such as acetonitrile, propionitrile and the like; halogenated solvents such as methylene chloride, chloroform and the like; aromatic hydrocarbons such as toluene, xylene and the like and mixtures thereof; preferable the one or more organic solvent is methanol.

The solution may be heated to dissolve the pazopanib hydrochloride. Typically, the solution may be heated at a temperature of at about 25° C. to about reflux temperature. Preferably, the solution is heated at about 25° C. to about 65° C.

Then the pure pazopanib hydrochloride is isolated by addition of hydrochloric acid or by addition of seed pazopanib hydrochloride to the reaction mass and cooling the reaction mass at a temperature of about 0° C. to about 5° C. for precipitation.

Then the pazopanib hydrochloride can be recovered by any conventional techniques known in the art, for example filtration. Typically, if stirring is involved, the temperature during stirring can range from about −10° C. to about 10° C., preferably at about −5° C. to about +5° C.

The resultant product may optionally be further dried. Drying can be suitably carried out in a tray dryer, vacuum oven, air oven and the like. The drying can be carried out at a temperature ranging from about 30° C. to about 40° C. The drying can be carried out for any desired time until the required product purity is achieved, e.g., a time period ranging from about 1 hour to about 10 hours.

Pazopanib hydrochloride recovered using the purification process of the present invention is crystalline form, particularly crystalline Form 1.

The present invention provides a pazopanib or a pharmaceutically acceptable salts thereof, preferably pazopanib hydrochloride obtained by the process described herein, having a purity of at least about 97%, as measured by HPLC, preferably at least about 98% as measured by HPLC, and more preferably at least about 99.5%, as measured by HPLC; and contains less than 20 ppm of formula III as measured by HPLC, preferably less than 10 ppm, as measured by HPLC.

The reported literature discloses process for the preparation of pazopanib or pharmaceutically acceptable salts thereof, particularly hydrochloride salt, which involves use of specific predefined particles of inorganic bases in the preparation of Formula II and Formula III is a key step, which process involves cumbersome techniques like milling, grinding etc makes the process uneconomical. In contrast, the process herein described arrives at a highly pure pazopanib hydrochloride, which includes bases without limiting to any specific particle size, thereby making the process more suitable for commercial applications.

In another embodiment, the present invention provides novel polymorphic Forms of pazopanib hydrochloride, processes for preparation thereof, and pharmaceutical compositions comprising one or more of such polymorphic Forms.

The polymorphic forms of pazopanib hydrochloride of the present invention have advantageous properties selected from at least one of: chemical purity, flowability, solubility, morphology or crystal habit, stability—such as storage stability, stability to dehydration, stability to polymorphic conversion, low hygroscopicity, and low content of residual solvents.

The term "solvate," as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount.

The polymorphic Forms of Pazopanib hydrochloride and polymorphic Forms of Formula III of the present invention obtained by process of present invention are characterized by one or more analytical methods such as X-ray powder diffraction (XRPD) patterns, differential scanning calorimetry (DSC) curves and thermo gravimetric analysis (TGA).

The X-Ray powder diffraction can be measured by an X-ray powder Diffractometer equipped with a Cu-anode ([λ]=1.54 Angstrom), X-ray source operated at 30 kV, 15 mA and a Ni filter is used to strip K-beta radiation. Two-theta calibration is performed using an NIST SRM 640c Si standard. The sample was analyzed using the following instrument parameters: measuring range=3-45° 2θ; step width=0.020°; and scan speed=5°/minute.

All DSC data reported herein were analyzed in hermitically sealed aluminium pan, with a blank hermitically sealed aluminium pan as the reference and were obtained using DSC (DSC Q200, TA instrumentation, Waters) at a scan rate of 10° C. per minute with an Indium standard.

All TGA data reported herein were analyzed using TGA Q500 V 20.2 build 27 in platinum pan with a temperature rise of about 10° C./min in the range of about 30° C. to about 250° C.

In another embodiment, the present invention provides novel polymorphic Forms of pazopanib hydrochloride; wherein the polymorphic Forms have been designated as pazopanib hydrochloride Form-L1, pazopanib hydrochloride Form-L2, pazopanib hydrochloride Form-L3, pazopanib hydrochloride Form-L4, pazopanib hydrochloride Form-L5, pazopanib hydrochloride Form-L6, pazopanib hydrochloride Form-L7, pazopanib hydrochloride Form-L8 and pazopanib hydrochloride Form-L9.

In another embodiment, the present invention provides pazopanib hydrochloride Form-L1.

In another embodiment, the present invention provides pazopanib hydrochloride Form-L1 characterized by a powder X-Ray diffraction (PXRD) pattern substantially in accordance with FIG. 1.

In another embodiment, the present invention provides pazopanib hydrochloride Form-L1 characterized by a PXRD pattern having peaks at about: 6.4, 7.0, 9.2, 11.5, 12.4, 14.1, 14.3, 15.8, 16.9, 17.8, 18.9, 19.1, 20.4, 20.7, 21.9, 22.8, 23.8, 24.5, 25.4, 26.7, 27.1, 28.0, 28.5, 29.1, 30.8, 31.3, 31.7, 32.0, 32.5, 33.9 and 35.5°±0.2° 2θ.

Figure 2:
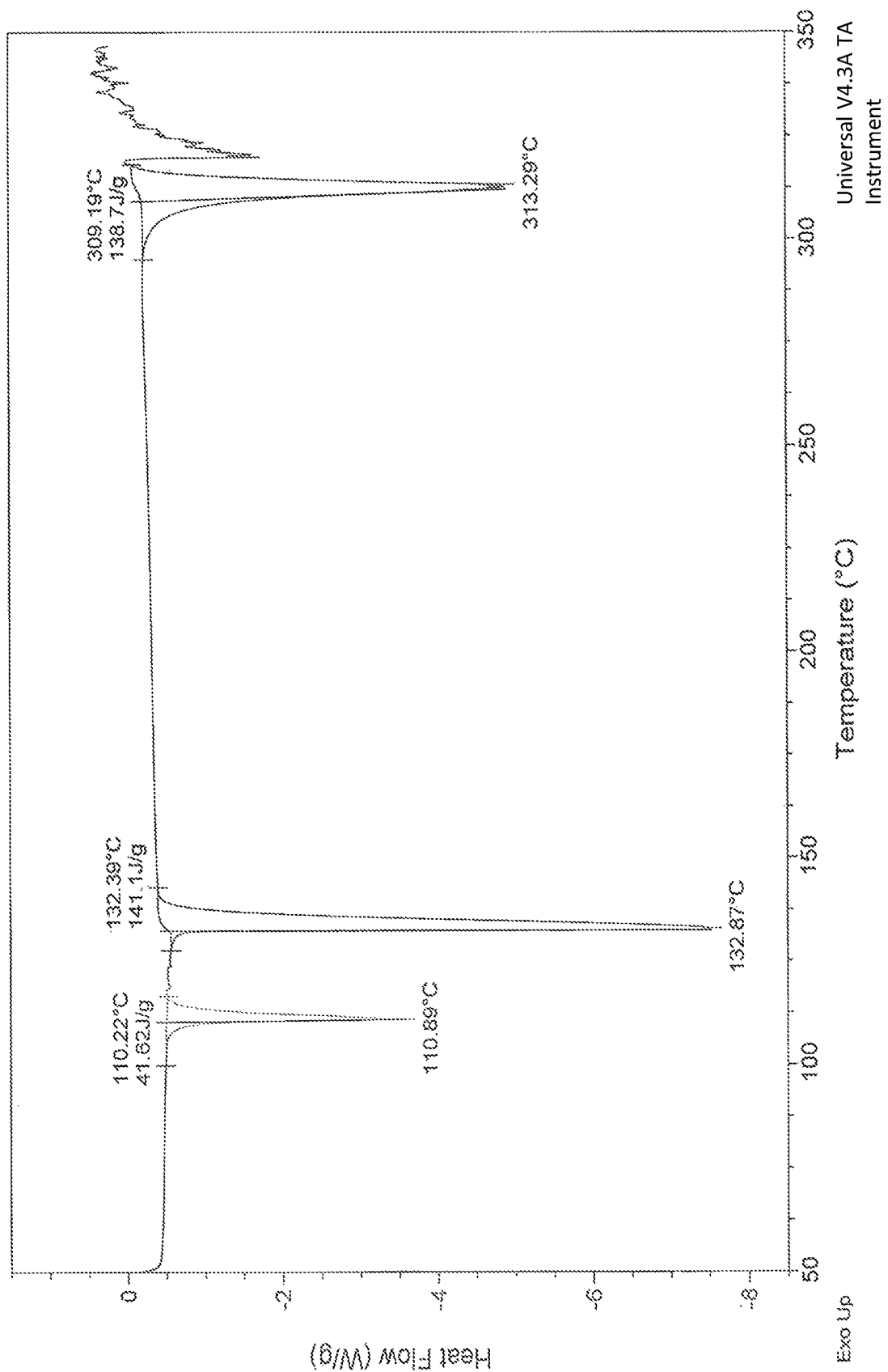
FIG. 2 is the characteristic differential scanning calorimetric (DSC) thermogram of Pazopanib hydrochloride Form-L1.

In another embodiment, the present invention provides pazopanib hydrochloride Form-L1 characterized by differential scanning calorimetry (DSC) substantially in accordance with FIG. 2.

Figure 3:
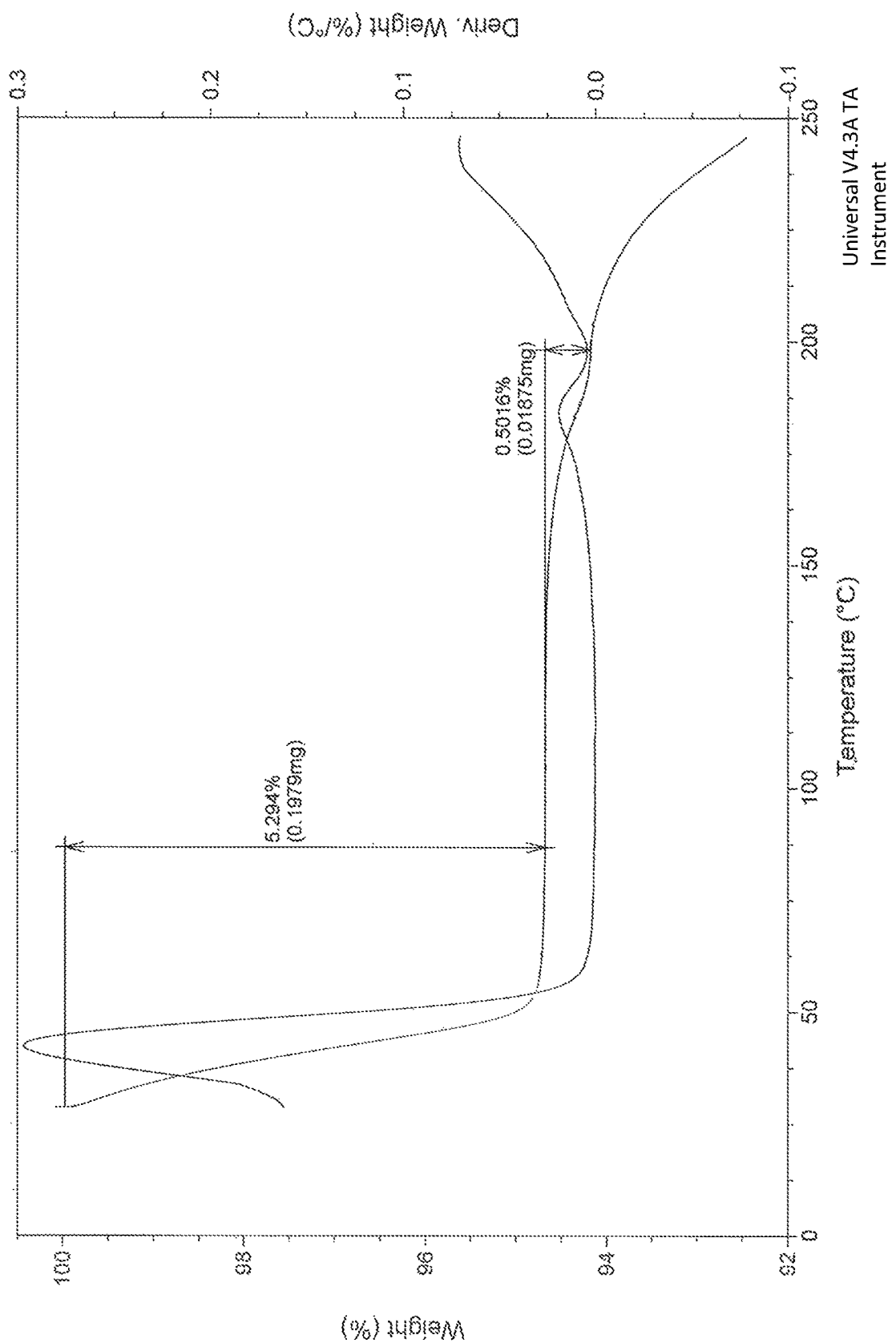
FIG. 3 is the characteristic thermo gravimetric analysis (TGA) of Pazopanib hydrochloride Form-L1.

In another embodiment, the present invention provides pazopanib hydrochloride Form-L1 characterized by thermo gravimetric analysis (TGA) substantially in accordance with FIG. 3.

In another embodiment, the present invention provides a process for preparation of pazopanib hydrochloride Form-L1, comprising:
a) providing a solution of pazopanib hydrochloride in an organic solvent (S4),
b) optionally combining the step a) reaction mass and an organic solvent (S5) at a temperature less than 0° C., and
c) isolating the pazopanib hydrochloride Form-L1.

The organic solvent (S4) and organic solvent (S5) may be same or different. The organic solvent (S4) & (S5) include, but are not limited to alcohols, halogenated solvents and mixtures thereof. Preferably, alcohols such as methanol, ethanol, isopropanol and the like; halogenated solvents such as methylene chloride, chloroform and the like; more preferably the organic solvent is methanol, methylene chloride and mixtures thereof.

The step a) of providing a solution of pazopanib hydrochloride in an organic solvent (S4) includes first heated to dissolve the pazopanib hydrochloride in an organic solvent (S4). Typically, the solution is heated at a temperature of at about 25° C. to about reflux temperature; preferably, at a temperature of at about 60° C. to about 65° C.

Then, optionally the resultant reaction solution can be added in to an organic solvent (S5) to precipitate out the product at a temperature less than 0° C.

The resultant reaction solution of step a) or step b) can be isolated by conventional techniques known in the art such as by cooling the solution to crystallization, concentrated by subjecting the solution to heating, spray drying, freeze drying, evaporation on rotary evaporator under vacuum, agitated thin film evaporator (ATFE) and the like; preferably cooling the solution to crystallization. Pazopanib hydrochloride From-L1 can be recovered by any conventional techniques known in the art, for example filtration.

In another embodiment, the present invention provides pazopanib hydrochloride Form-L2.

Figure 4:
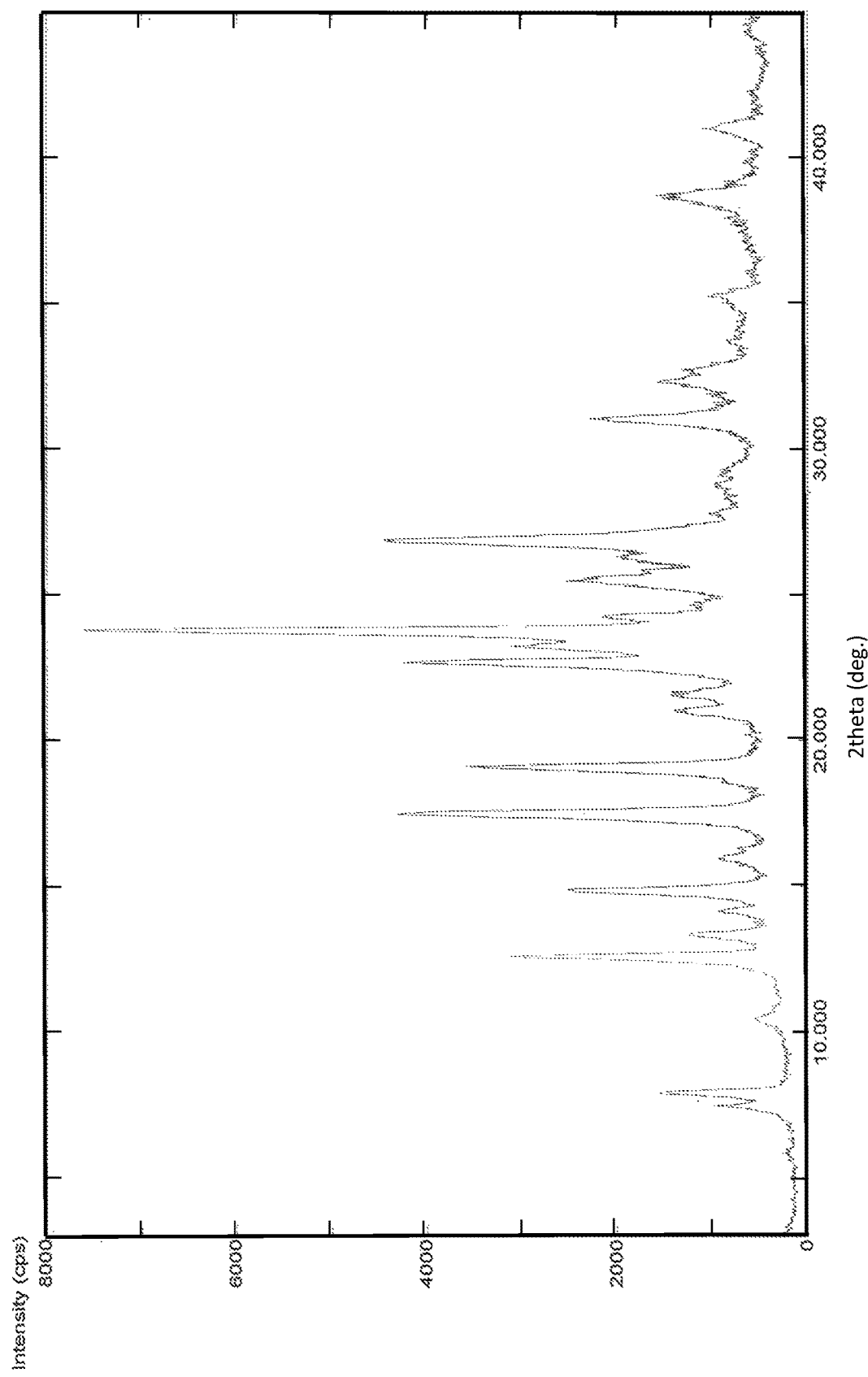
FIG. 4 is the characteristic powder X-ray diffraction (XRD) pattern of Pazopanib hydrochloride Form-L2.

In another embodiment, the present invention provides pazopanib hydrochloride Form-L2 characterized by a powder X-Ray diffraction (PXRD) pattern substantially in accordance with FIG. 4.

In another embodiment, the present invention provides pazopanib hydrochloride Form-L2 characterized by a PXRD pattern having peaks at about: 7.4, 7.9, 10.4, 12.5, 13.3, 14.1, 14.8, 15.9, 17.4, 19.0, 21.0, 21.5, 22.6, 23.2, 23.7, 24.2, 25.4, 25.8, 26.2, 26.8, 31.0, 32.3 and 32.6°±0.2° 2θ.

In another embodiment, the present invention provides a process for preparation of pazopanib hydrochloride Form-L2, comprising:
a) providing a solution of pazopanib hydrochloride in methanol,
b) cooling the solution to precipitation, and
c) isolating the pazopanib hydrochloride From-L2.

The step a) of providing a solution of pazopanib hydrochloride in methanol includes heating to dissolve the pazopanib hydrochloride in methanol at a temperature of about 25° C. to about reflux temperature; preferably at about 55° C. to about 65° C. Then, the resultant reaction solution can be cooled to precipitation at about 0° C. to about 5° C. The precipitated pazopanib hydrochloride From-L2 can be recovered by any conventional techniques known in the art, for example filtration.

In another embodiment, the present invention provides pazopanib hydrochloride Form-L3.

Figure 5:
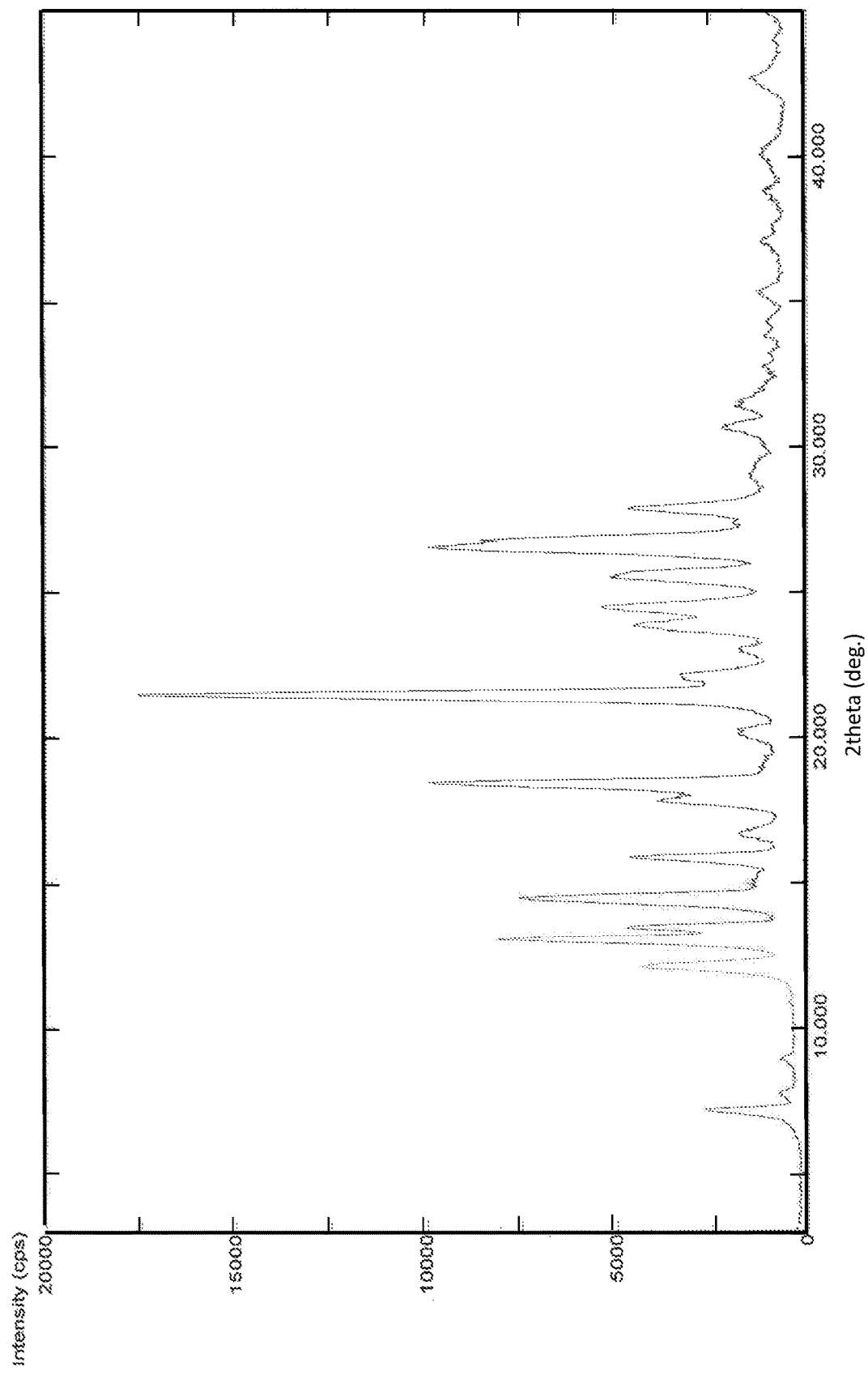
FIG. 5 is the characteristic powder X-ray diffraction (XRD) pattern of Pazopanib hydrochloride Form-L3.

In another embodiment, the present invention provides pazopanib hydrochloride Form-L3 characterized by a powder X-Ray diffraction (PXRD) pattern substantially in accordance with FIG. 5.

In another embodiment, the present invention provides pazopanib hydrochloride Form-L3 characterized by a PXRD pattern having peaks at about: 7.1, 7.6, 12.0, 13.0, 13.4, 14.4, 15.8, 16.6, 17.7, 18.4, 20.1, 21.4, 22.1, 22.9, 23.7, 24.4, 25.4, 26.4, 26.7, 27.8, 30.5 and 31.3°±0.2° 2θ.

Figure 6:
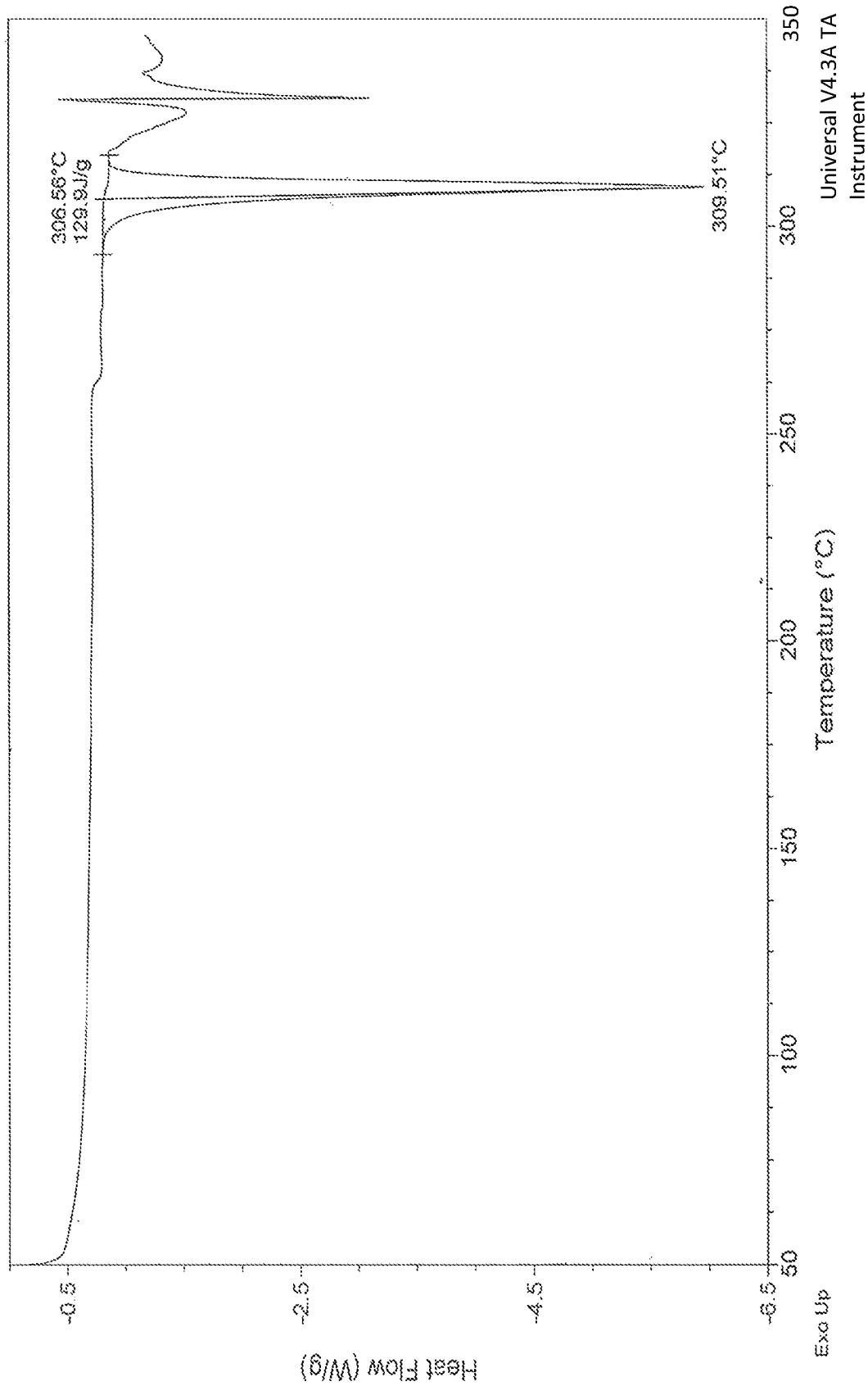
FIG. 6 is the characteristic differential scanning calorimetric (DSC) thermogram of Pazopanib hydrochloride Form-L3.

In another embodiment, the present invention provides pazopanib hydrochloride Form-L3 characterized by differential scanning calorimetry (DSC) substantially in accordance with FIG. 6.

In another embodiment, the present invention provides a process for preparation of pazopanib hydrochloride Form-L3, comprising:
a) providing a solution of pazopanib hydrochloride in water,
b) cooling the solution to precipitation, and
c) isolating the pazopanib hydrochloride From-L3.

The step a) of providing a solution of pazopanib hydrochloride in water, which process includes heating to dissolve the pazopanib hydrochloride in water at a temperature of about 25° C. to about reflux temperature; preferably at about 90° C. to about 100° C. Then, the resultant reaction solution can be cooled to precipitation at less than 30° C. The precipitated pazopanib hydrochloride From-L3 can be recovered by any conventional techniques known in the art, for example filtration. Typically, if stirring is involved, the temperature during stirring can range from about 0° C. to about 5° C. The resultant product may optionally be further dried at suitable temperatures i.e. about 30° C. to about 80° C.

In another embodiment, the present invention provides pazopanib hydrochloride Form-L4.

In another embodiment, pazopanib hydrochloride ethanol solvate, designated as Form-L4.

Figure 7:
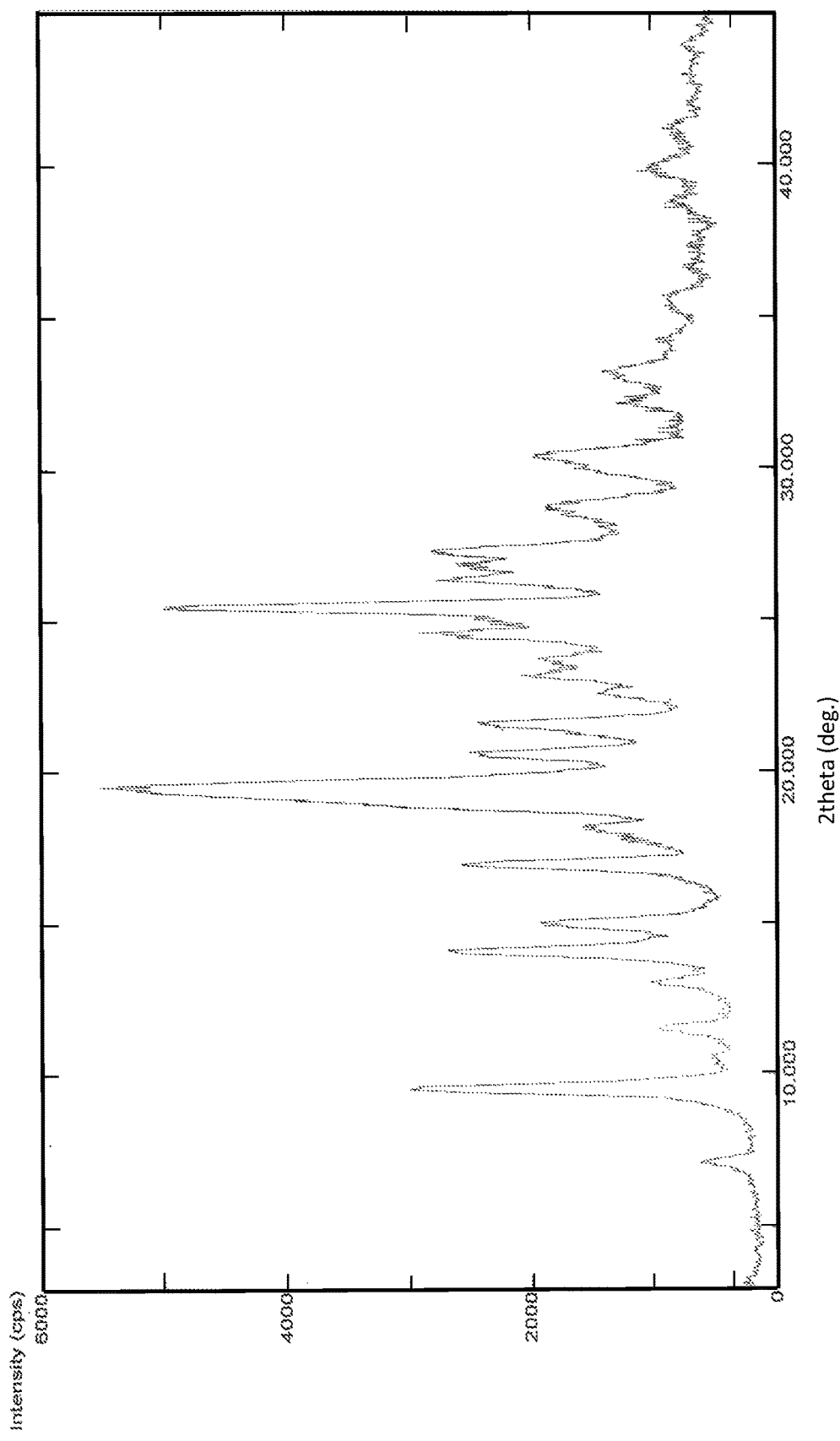
FIG. 7 is the characteristic powder X-ray diffraction (XRD) pattern of Pazopanib hydrochloride Form-L4.

In another embodiment, the present invention provides pazopanib hydrochloride Form-L4 characterized by a powder X-ray diffraction (PXRD) pattern substantially in accordance with FIG. 7.

In another embodiment, the present invention provides pazopanib hydrochloride Form-L4 characterized by a PXRD pattern having peaks at about: 7.1, 9.5, 11.5, 13.0, 14.1, 15.0, 16.9, 17.7, 18.1, 19.5, 20.6, 21.6, 22.6, 23.1, 23.7, 24.5, 25.4, 26.3, 26.8, 27.3, 28.7, 30.3, 32.1, 33.2, 34.2 and 35.5°±0.2° 2θ.

Figure 8:
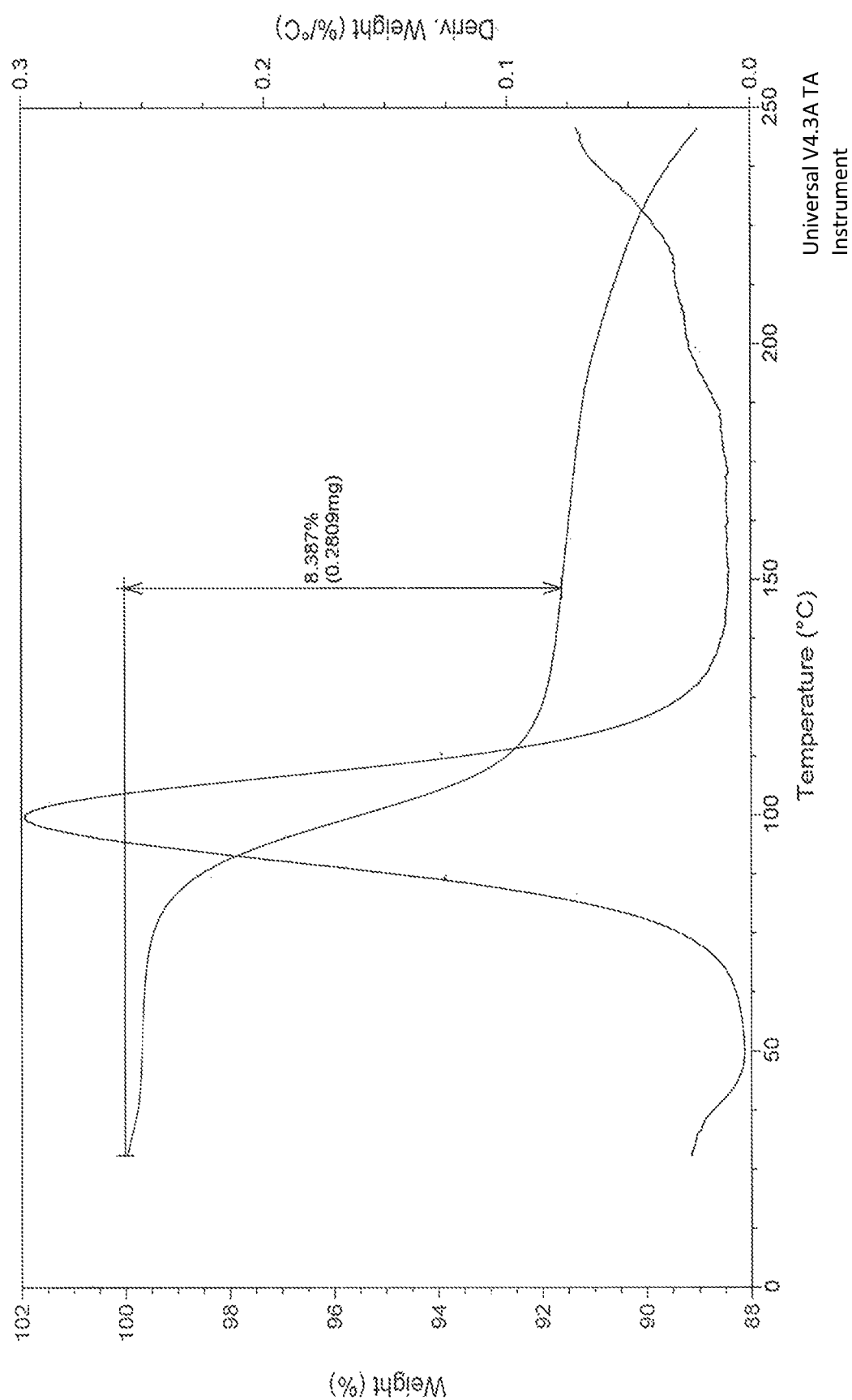
FIG. 8 is the characteristic thermo gravimetric analysis (TGA) of Pazopanib hydrochloride Form-L4.

In another embodiment, the present invention provides pazopanib hydrochloride Form-L4 characterized by thermo gravimetric analysis (TGA) substantially in accordance with FIG. 8.

In another embodiment, the present invention provides a process for preparation of pazopanib hydrochloride Form-L4, comprising:
a) providing a solution of pazopanib hydrochloride in ethanol
b) combining the step a) reaction mass and an additional ethanol at a temperature less than 0° C., and
c) isolating the pazopanib hydrochloride Form-L4.

The step a) of providing a solution of pazopanib hydrochloride in ethanol includes first heating to about 25° C. to about reflux temperature. Preferably, the solution is heated at about 70° C. to about 80° C. and then the resultant reaction solution can be isolated by conventional techniques known in the art such as isolated by solvent precipitation, crystallization, concentrated by subjecting the solution to heating, spray drying, freeze drying, evaporation on rotary evaporator under vacuum, agitated thin film evaporator (ATFE) and the like; preferably solvent precipitation method by adding the above obtained clear solution to a pre-chilled ethanol at a temperature of less than 0° C.; preferably at about −15° C. to about −10° C. Pazopanib hydrochloride Form-L4 can be recovered by any conventional techniques known in the art, for example filtration.

In another embodiment, the present invention provides pazopanib hydrochloride Form-L5.

In another embodiment, the present invention provides pazopanib hydrochloride n-propanol solvate, designated as Form-L5.

Figure 9:
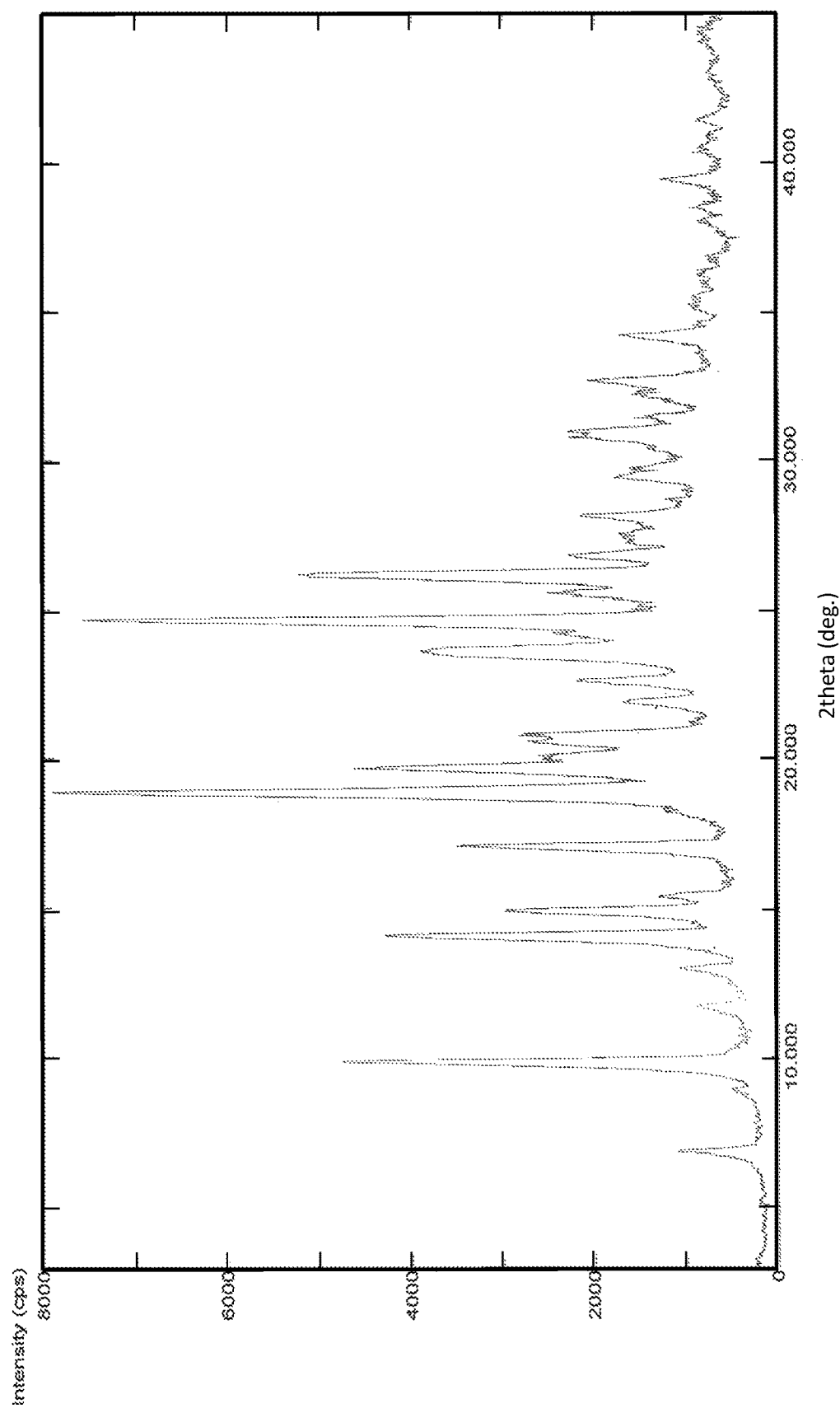
FIG. 9 is the characteristic powder X-ray diffraction (XRD) pattern of Pazopanib hydrochloride Form-L5.

In another embodiment, the present invention provides pazopanib hydrochloride Form-L5 characterized by a powder X-Ray diffraction (PXRD) pattern substantially in accordance with FIG. 9.

In another embodiment, the present invention provides pazopanib hydrochloride Form-5 characterized by a PXRD pattern having peaks at about: 6.8, 8.9, 9.8, 11.6, 12.9, 14.0, 14.9, 15.4, 17.0, 18.2, 18.8, 19.6, 20.1, 20.5, 20.8, 21.8, 22.6, 23.5, 24.1, 24.6, 25.5, 26.1, 26.7, 27.4, 28.1, 29.4, 30.7, 30.9, 31.4, 32.1, 32.6 and 34.1°±0.2° 2θ.

Figure 10:
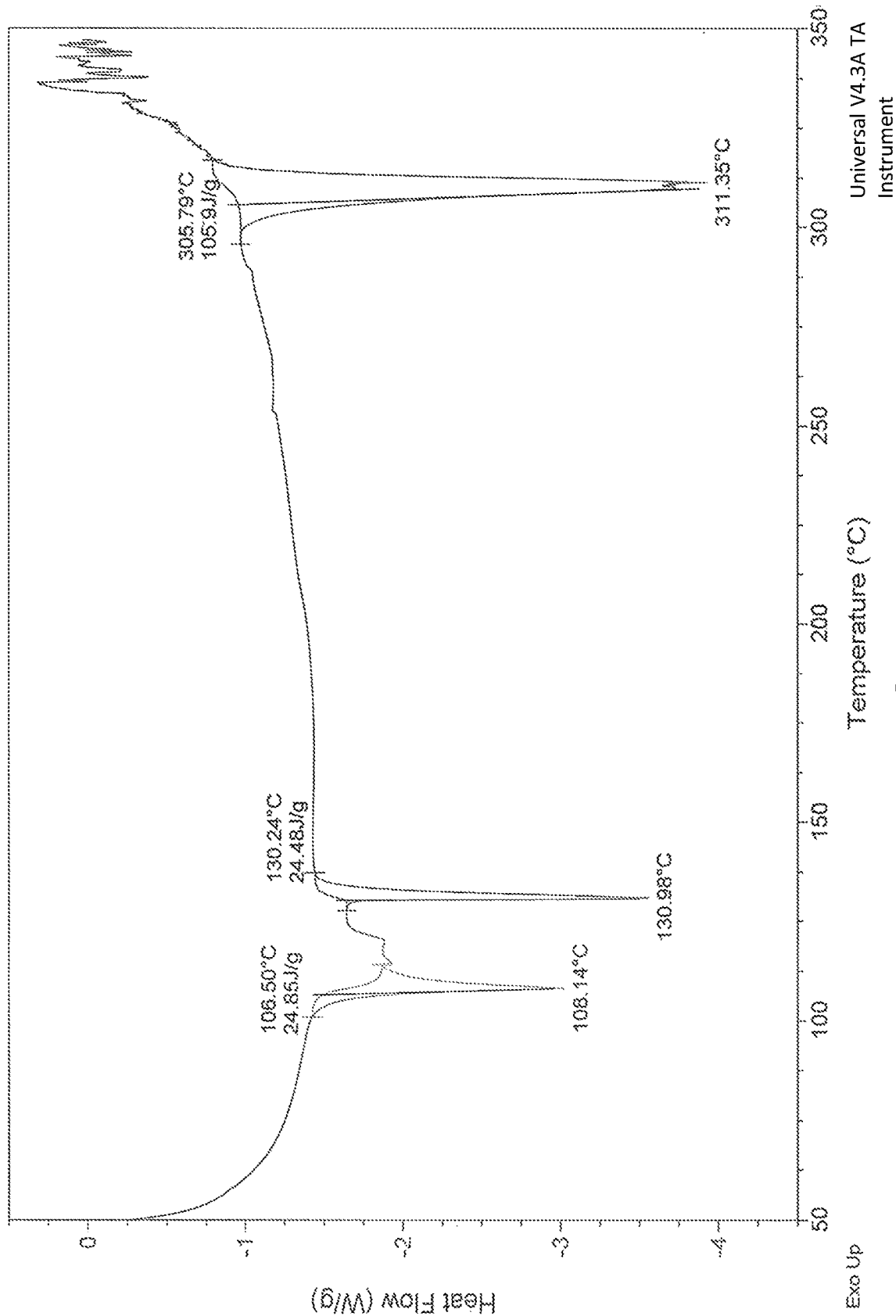
FIG. 10 is the characteristic differential scanning calorimetric (DSC) thermogram of Pazopanib hydrochloride Form-L5.

In another embodiment, the present invention provides pazopanib hydrochloride Form-L5 characterized by differential scanning calorimetry (DSC) substantially in accordance with FIG. 10.

Figure 11:
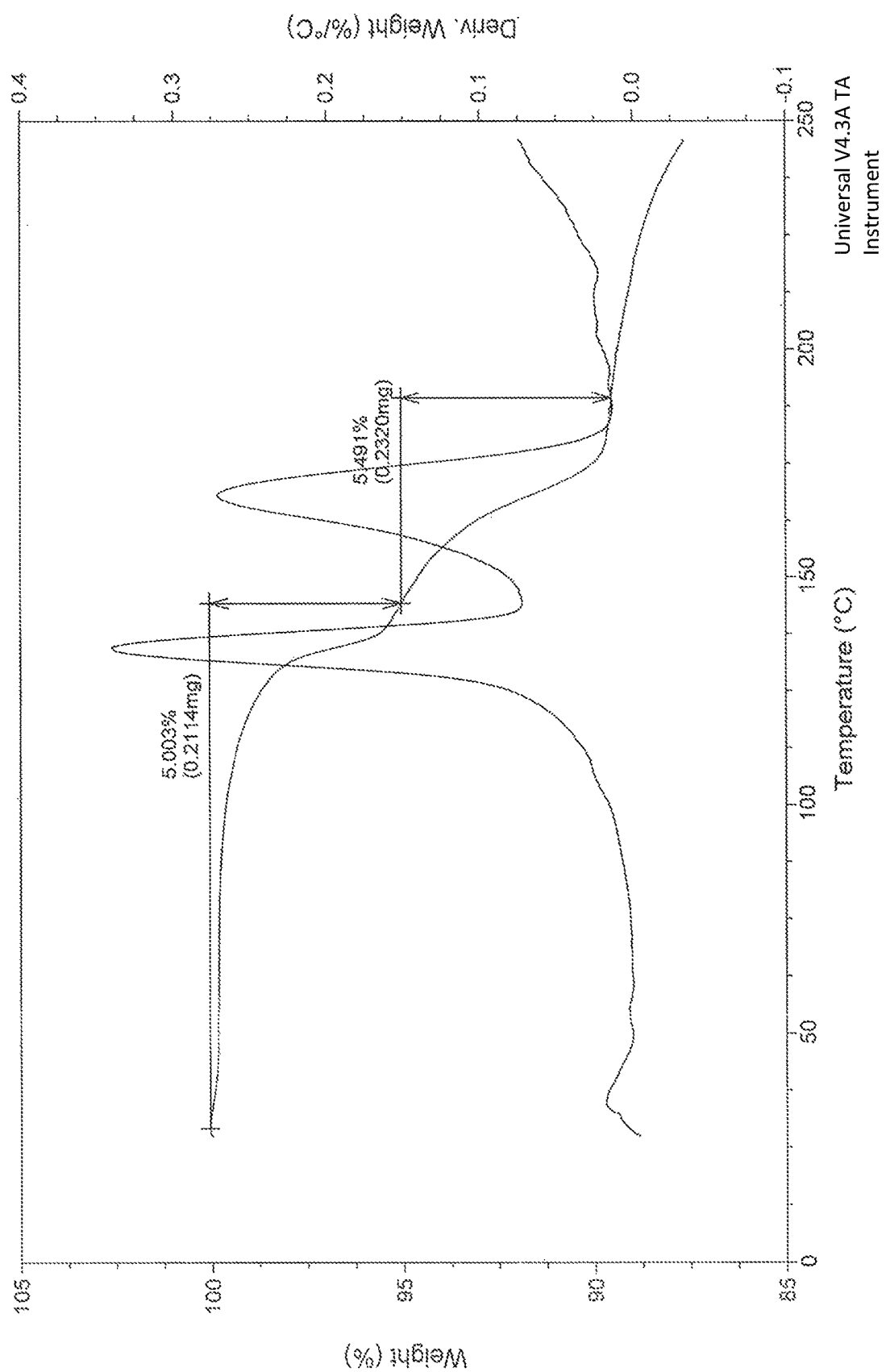
FIG. 11 is the characteristic thermo gravimetric analysis (TGA) of Pazopanib hydrochloride Form-L5.

In another embodiment, the present invention provides pazopanib hydrochloride Form-L5 characterized by thermo gravimetric analysis (TGA) substantially in accordance with FIG. 11.

In another embodiment, the present invention provides a process for preparation of pazopanib hydrochloride Form-L5, comprising:
a) providing a solution of pazopanib hydrochloride in n-propanol,
b) combining the step a) reaction mass and an additional n-propanol at a temperature less than 0° C., and
c) isolating the pazopanib hydrochloride Form-L5.

The step a) of providing a solution of pazopanib hydrochloride in n-propanol includes first heating to about 25° C. to about reflux temperature. Preferably, the solution is heated at about 90° C. to about 100° C. and then the resultant reaction solution can be isolated by conventional techniques known in the art such as isolated by solvent precipitation, crystallization, concentrated by subjecting the solution to heating, spray drying, freeze drying, evaporation on rotary evaporator under vacuum, agitated thin film evaporator (ATFE) and the like; preferably solvent precipitation method by adding the above obtained clear solution to a pre-chilled n-propanol at a temperature of less than 0° C.; preferably at about −15° C. to about −10° C. Pazopanib hydrochloride Form-L5 can be recovered by any conventional techniques known in the art, for example filtration.

In another embodiment, the present invention provides pazopanib hydrochloride Form-L6.

In another embodiment, the present invention provides pazopanib hydrochloride n-butanol solvate, designated as Form-L6.

Figure 12:
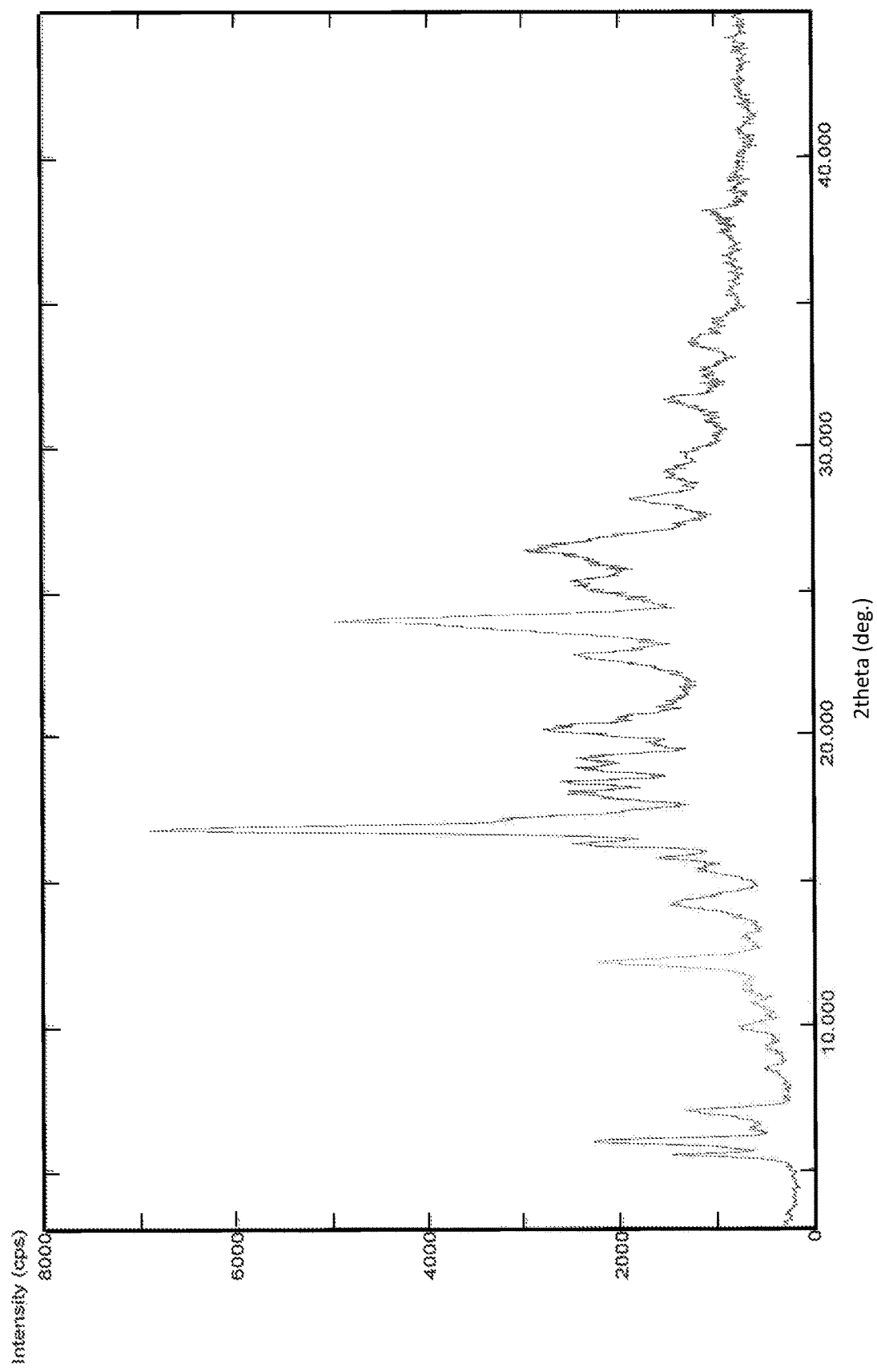
FIG. 12 is the characteristic powder X-ray diffraction (XRD) pattern of Pazopanib hydrochloride Form-L6.

In another embodiment, the present invention provides pazopanib hydrochloride Form-L6 characterized by a powder X-Ray diffraction (PXRD) pattern substantially in accordance with FIG. 12.

In another embodiment, the present invention provides pazopanib hydrochloride Form-L6 characterized by an X-Ray diffraction (XRD) pattern having peaks at about: 5.5, 6.0, 7.0, 8.4, 9.8, 10.6, 11.1, 12.1, 12.9, 14.1, 15.3, 15.7, 16.2, 16.7, 17.1, 17.9, 18.3, 18.7, 19.1, 20.1, 20.5, 22.7, 23.9, 25.2, 26.3, 28.1, 29.0, 31.6 and 33.5°±0.2° 2θ.

Figure 13:
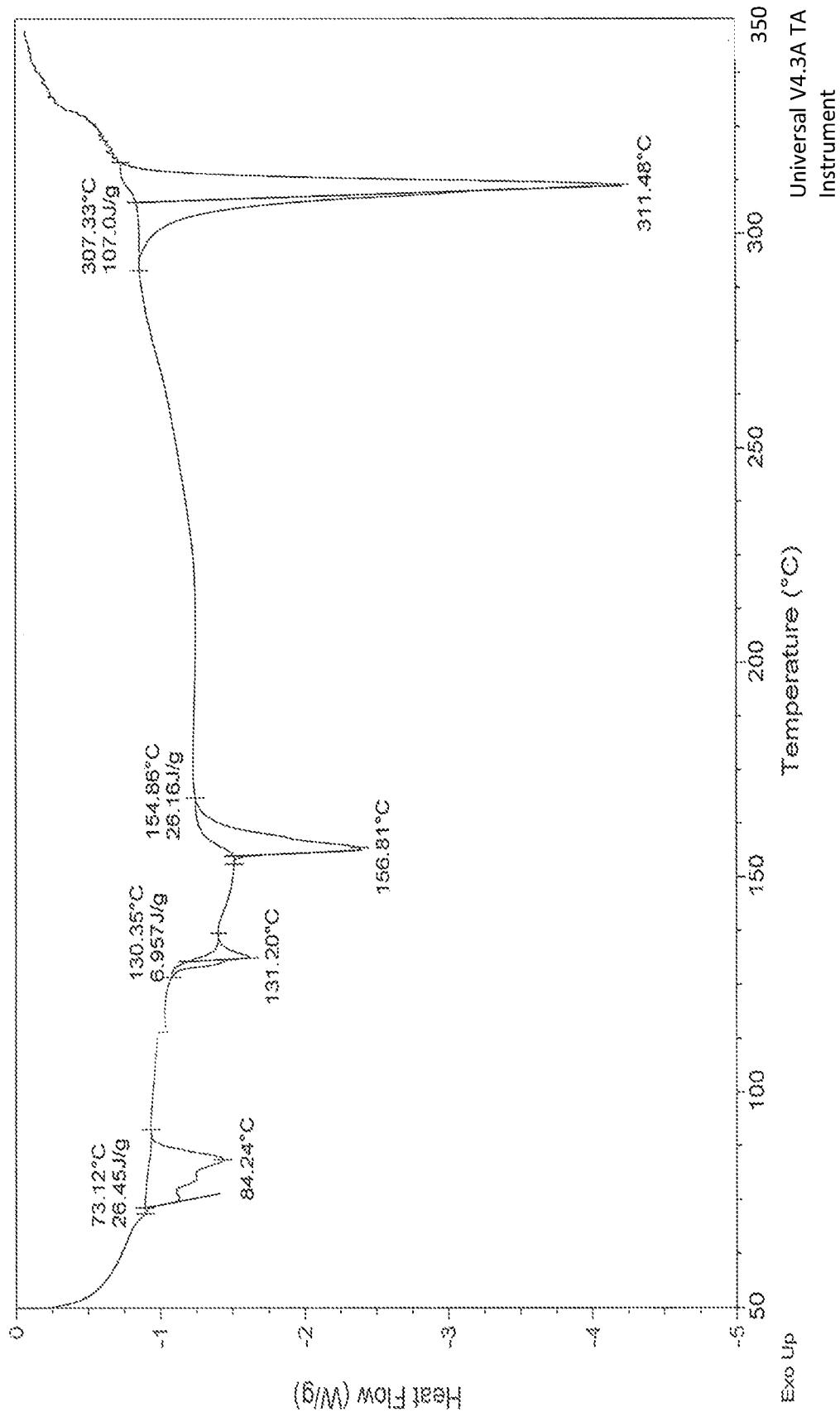
FIG. 13 is the characteristic differential scanning calorimetric (DSC) thermogram of Pazopanib hydrochloride Form-L6.

In another embodiment, the present invention provides pazopanib hydrochloride Form-L6 characterized by differential scanning calorimetry (DSC) substantially in accordance with FIG. 13.

Figure 14:
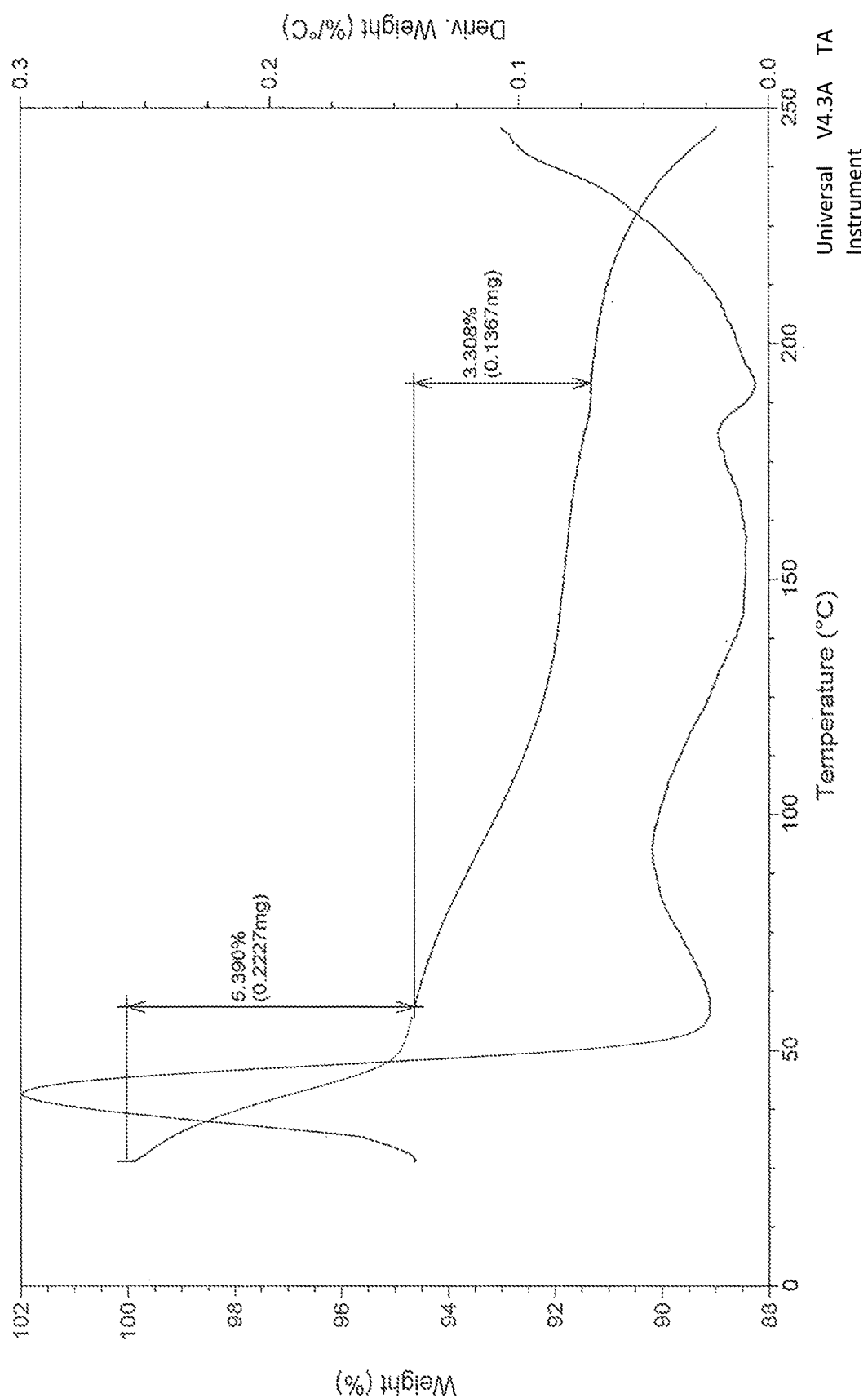
FIG. 14 is the characteristic thermo gravimetric analysis (TGA) of Pazopanib hydrochloride Form-L6.

In another embodiment, the present invention provides pazopanib hydrochloride Form-L6 characterized by thermo gravimetric analysis (TGA) substantially in accordance with FIG. 14.

In another embodiment, the present invention provides a process for preparation of pazopanib hydrochloride Form-6, comprising:
a) providing a solution of pazopanib hydrochloride in n-butanol,
b) combining the step a) reaction mass and an additional n-butanol at a temperature less than 0° C., and
c) isolating the pazopanib hydrochloride Form-L6.

The step a) of providing a solution of pazopanib hydrochloride in n-butanol includes first heating to about 25° C. to about reflux temperature. Preferably, the solution is heated at about 110° C. to about 120° C. and then the resultant reaction solution can be isolated by conventional techniques known in the art such as isolated by solvent precipitation, crystallization, concentrated by subjecting the solution to heating, spray drying, freeze drying, evaporation on rotary evaporator under vacuum, agitated thin film evaporator (ATFE) and the like; preferably solvent precipitation method by adding the above obtained clear solution to a pre-chilled n-butanol at a temperature of less than 0° C.; preferably at about −15° C. to about −10° C. Pazopanib hydrochloride Form-L6 can be recovered by any conventional techniques known in the art, for example filtration.

In another embodiment, the present invention provides pazopanib hydrochloride Form-L7.

In another embodiment, the present invention provides pazopanib hydrochloride 2-butanol solvate, designated as Form-L7.

Figure 15:
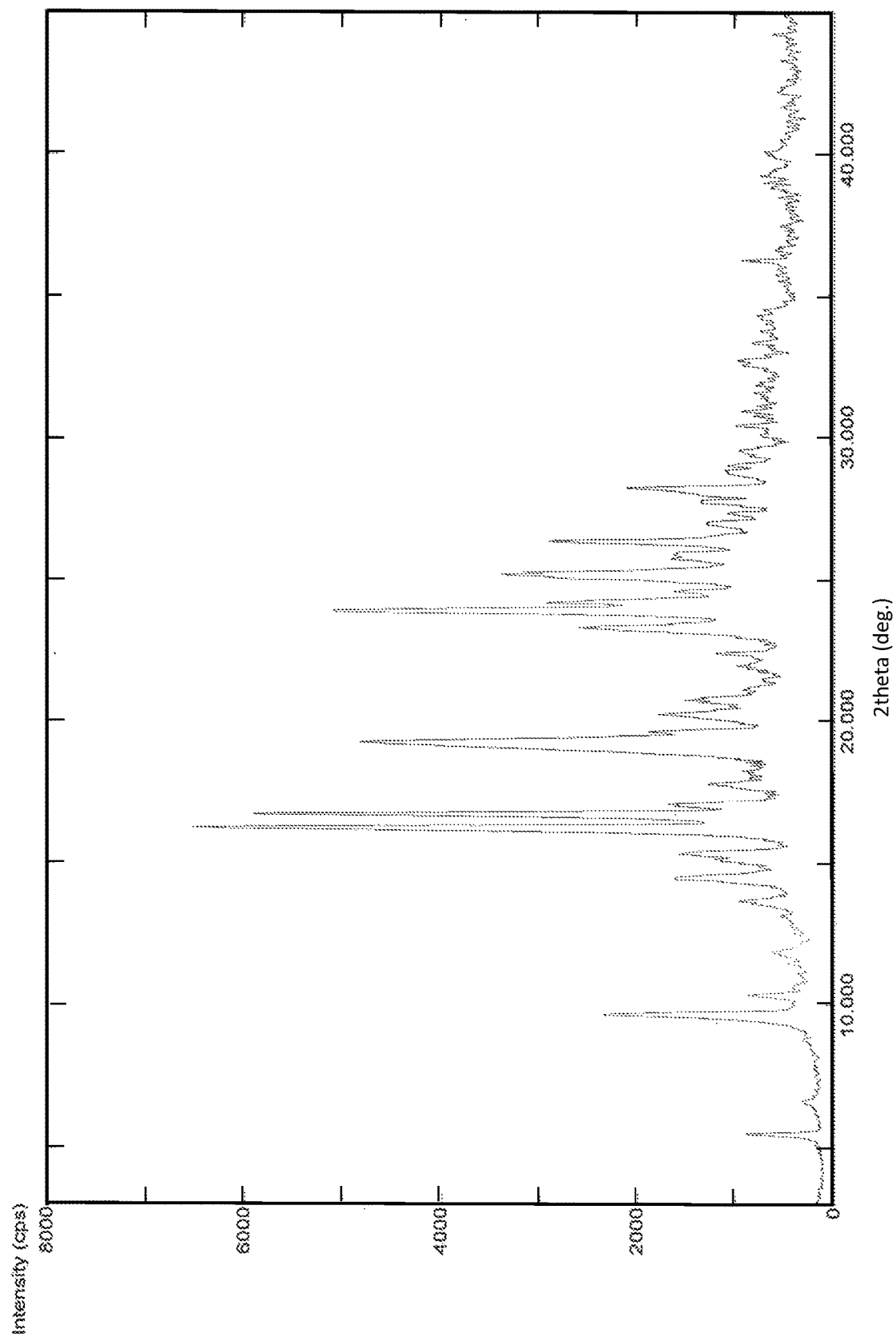
FIG. 15 is the characteristic powder X-ray diffraction (XRD) pattern of Pazopanib hydrochloride Form-L7.

In another embodiment, the present invention provides pazopanib hydrochloride Form-L7 characterized by a powder X-Ray diffraction (PXRD) pattern substantially in accordance with FIG. 15.

In another embodiment, the present invention provides pazopanib hydrochloride Form-L7 characterized by an X-Ray diffraction (XRD) pattern having peaks at about: 5.5, 6.6, 9.6, 10.3, 11.8, 13.6, 14.4, 15.3, 16.2, 16.7, 17.0, 17.7, 19.2, 19.6, 20.2, 20.7, 21.9, 22.4, 23.3, 23.8, 24.1, 24.5, 25.1, 25.8, 26.3, 26.9, 27.3, 27.7, 28.2, 28.8, 29.0, 29.5, 30.4 and 30.9°±0.2° 2θ.

In another embodiment, the present invention provides a process for preparation of pazopanib hydrochloride Form-L7, comprising:
a) providing a solution of pazopanib hydrochloride in 2-butanol,
b) combining the step a) reaction mass and an additional 2-butanol at a temperature less than 0° C., and
c) isolating the pazopanib hydrochloride Form-L7.

The step a) of providing a solution of pazopanib hydrochloride in 2-butanol includes first heating to about 25° C. to about reflux temperature. Preferably, the solution is heated at about 90° C. to about 100° C. and then the resultant reaction solution can be isolated by conventional techniques known in the art such as isolated by solvent precipitation, crystallization, concentrated by subjecting the solution to heating, spray drying, freeze drying, evaporation on rotary evaporator under vacuum, agitated thin film evaporator (ATFE) and the like; preferably solvent precipitation method by adding the above obtained clear solution to a pre-chilled 2-butanol at a temperature of less than 0° C.; preferably at about −15° C. to about −10° C. Pazopanib hydrochloride Form-L7 can be recovered by any conventional techniques known in the art, for example filtration.

As used herein above, the starting material pazopanib hydrochloride for preparation of Form L1 to L7 is known in the art and can be prepared by any known method. The starting pazopanib hydrochloride may be any crystalline or other form of pazopanib hydrochloride, including various solvates and hydrates, as long as intended pazopanib hydrochloride polymorphs are produced during the process of the invention or pazopanib hydrochloride obtaining an existing solution from a previous processing step.

In another embodiment, the present invention provides pazopanib hydrochloride Form-L8.

In another embodiment, the present invention provides pazopanib hydrochloride tert-butanol solvate, designated as Form-L8.

Figure 16:
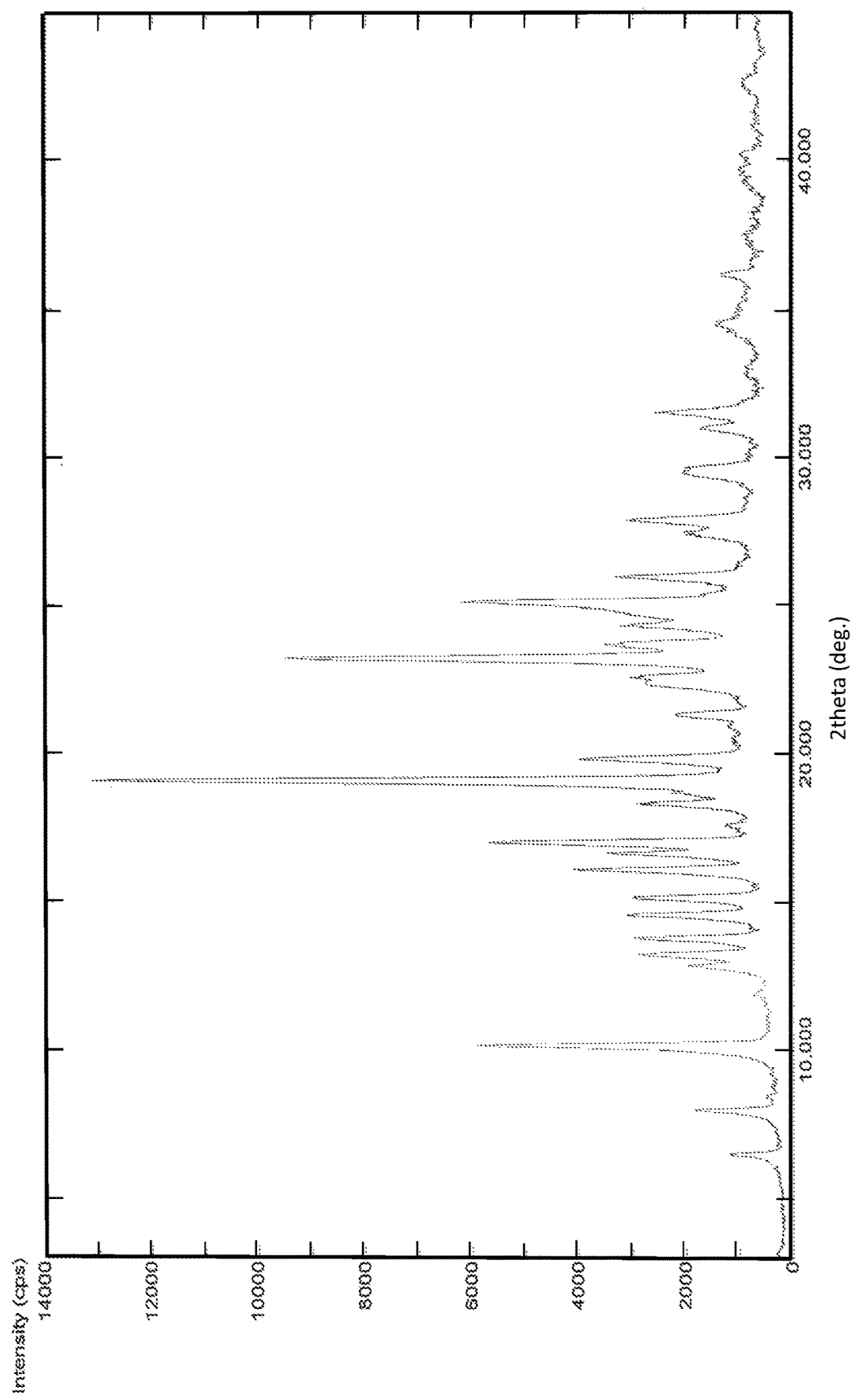
FIG. 16 is the characteristic powder X-ray diffraction (XRD) pattern of Pazopanib hydrochloride Form-L8.

In another embodiment, the present invention provides pazopanib hydrochloride Form-L8 characterized by a powder X-Ray diffraction (PXRD) pattern substantially in accordance with FIG. 16.

In another embodiment, the present invention provides pazopanib hydrochloride Form-L8 characterized by a PXRD pattern having peaks at about: 6.4, 7.9, 10.1, 12.8, 13.2, 13.7, 14.5, 15.1, 16.0, 16.6, 17.0, 17.5, 18.3, 18.6, 19.1, 19.8, 21.3, 22.2, 22.5, 23.2, 23.6, 24.2, 25.1, 25.98, 27.36, 27.8, 29.4, 30.9, 31.5, 34.4 and 36.2°±0.2° 2θ.

Figure 17:
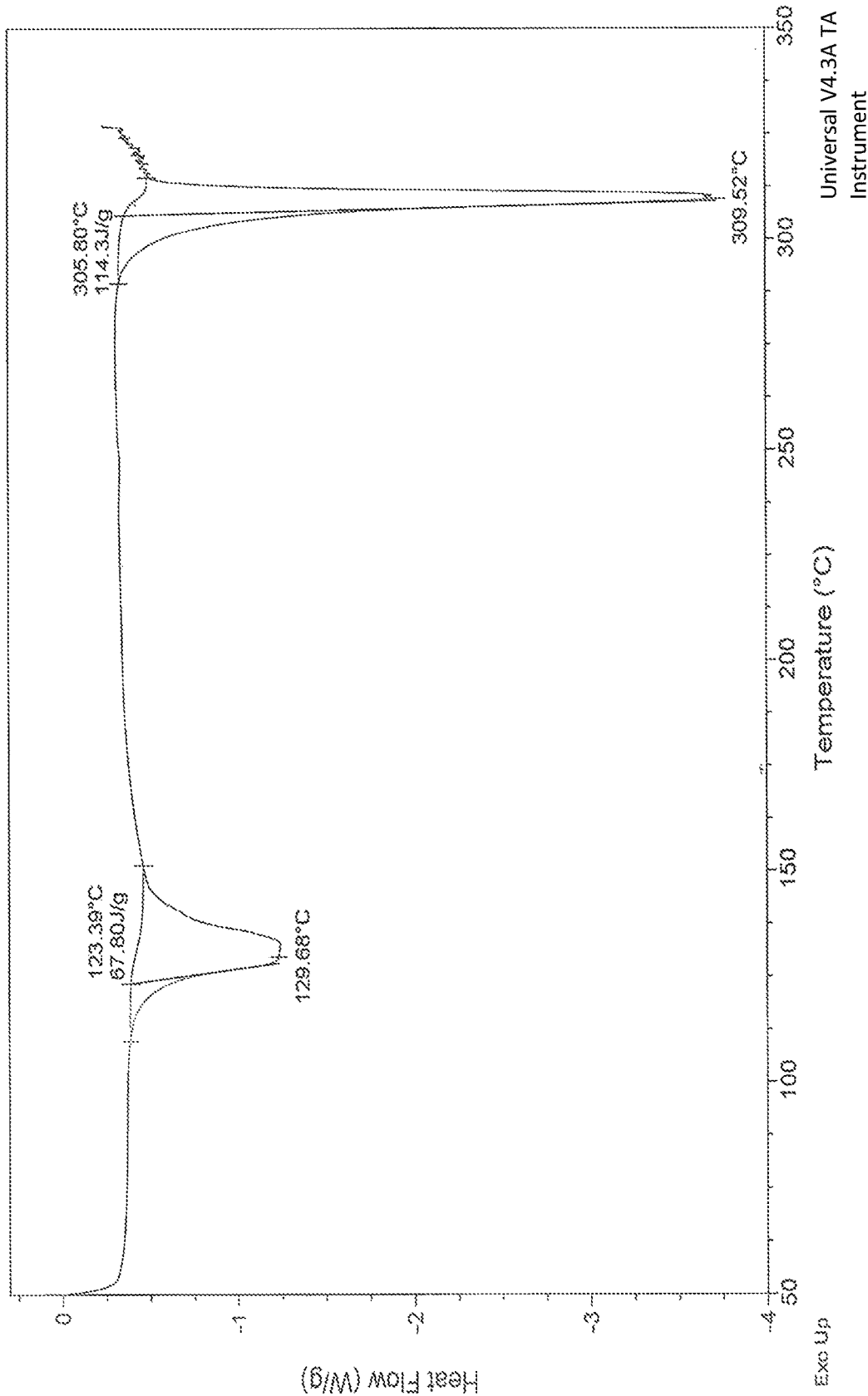
FIG. 17 is the characteristic differential scanning calorimetric (DSC) thermogram of Pazopanib hydrochloride Form-L8.

In another embodiment, the present invention provides pazopanib hydrochloride Form-L8 characterized by differential scanning calorimetry (DSC) substantially in accordance with FIG. 17.

Figure 18:
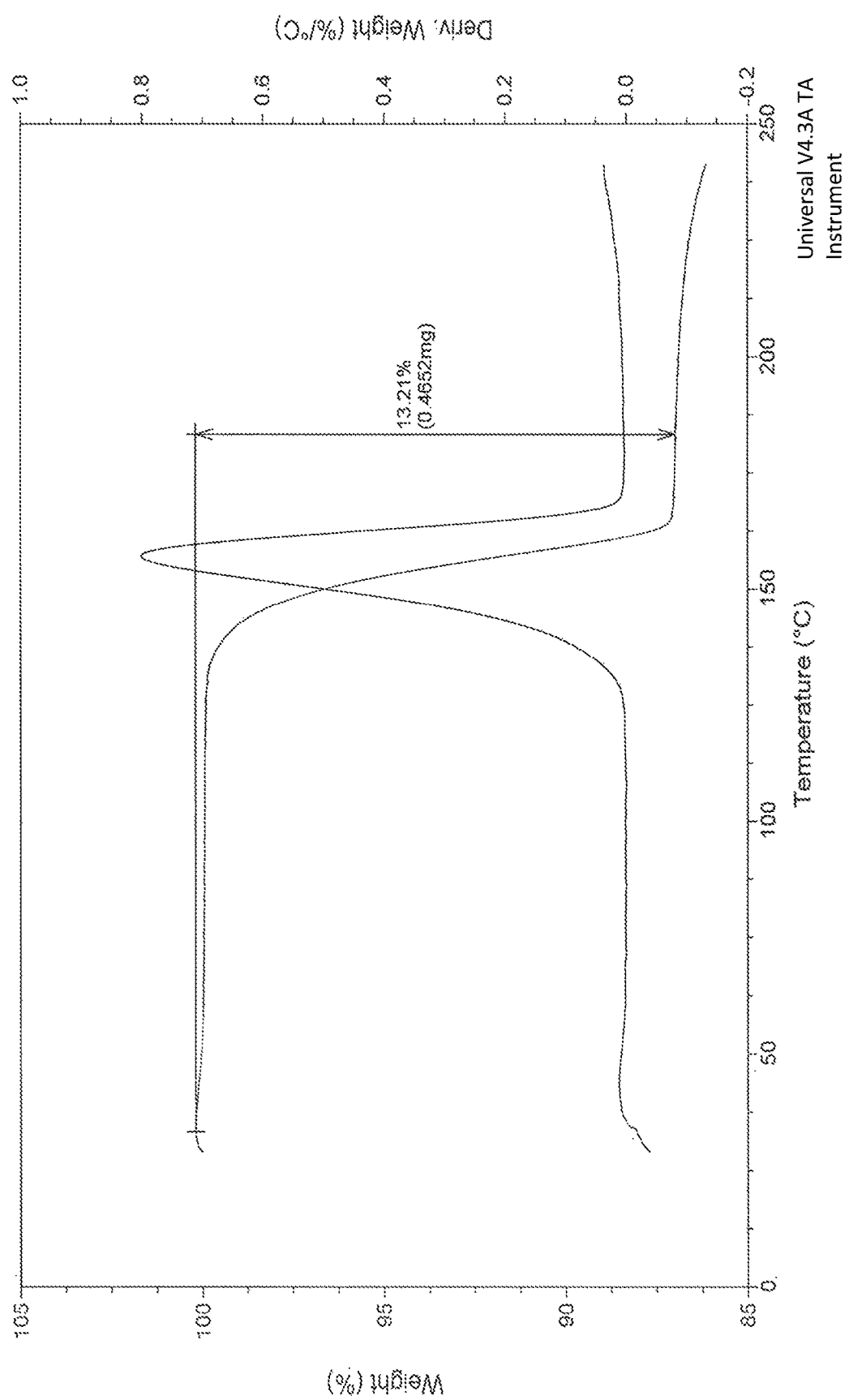
FIG. 18 is the characteristic thermo gravimetric analysis (TGA) of Pazopanib hydrochloride Form-L8.

In another embodiment, the present invention provides pazopanib hydrochloride Form-L8 characterized by thermo gravimetric analysis (TGA) substantially in accordance with FIG. 18.

In another embodiment, the present invention provides a process for preparation of pazopanib hydrochloride Form-L8, comprising:
 a) condensation of a compound of Formula III and Formula C in tert-butanol in presence of catalytic amount of hydrochloric acid,
 b) heating the reaction mass to about reflux,
 c) stirring the step b) solution for about 8 to 12 hours,
 d) cooling the solution to precipitation, and
 e) isolating the pazopanib hydrochloride Form-L8.

The starting material compound of Formula III and Formula C are known in the art and can be prepared by any known method or obtained by the processes herein described in the present specification.

The condensation of compound of Formula III and Formula C in presence of catalytic amount of hydrochloric acid is carried out at a temperature of about 25° C. to about reflux temperature; preferably at about 75° C. to about 85° C.

After completion of the reaction, the resultant reaction solution may be cooled at a temperature of about 25° C. to about 30° C. to precipitating pazopanib hydrochloride Form-L8. The pazopanib hydrochloride Form-L8 can be recovered by any conventional techniques known in the art, for example filtration.

In another embodiment, the present invention provides pazopanib hydrochloride Form-L9.

In another embodiment, the present invention provides pazopanib hydrochloride hemi tert-butanol solvate, designated as Form-L9.

Figure 19:
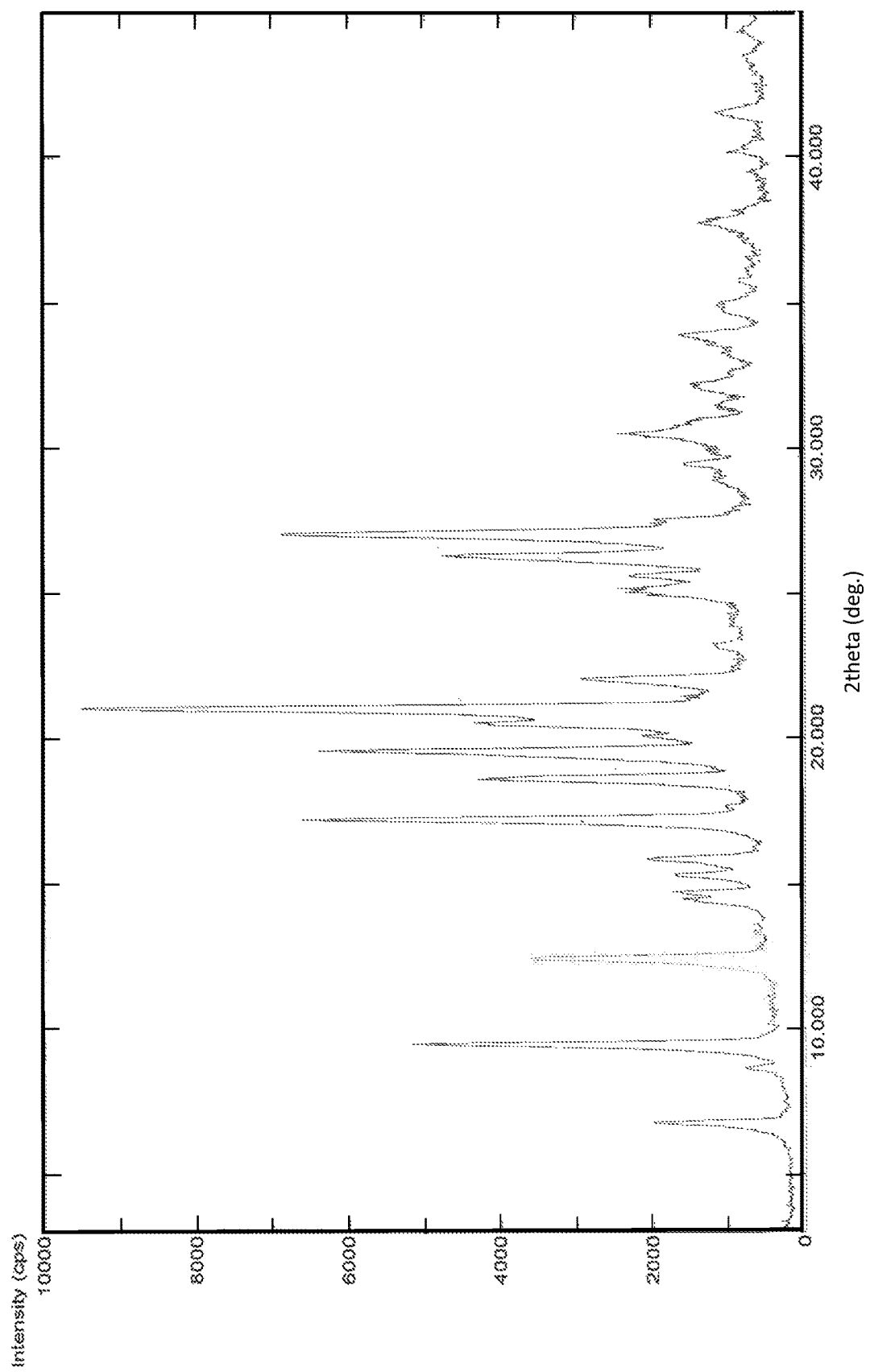
FIG. 19 is the characteristic powder X-ray diffraction (XRD) pattern of Pazopanib hydrochloride Form-L9.

In another embodiment, the present invention provides pazopanib hydrochloride Form-L9 characterized by a powder X-Ray diffraction (PXRD) pattern substantially in accordance with FIG. 19.

In another embodiment, the present invention provides pazopanib hydrochloride Form-L9 characterized by an X-Ray diffraction (XRD) pattern having peaks at about: 6.7, 8.7, 9.4, 12.4, 14.4, 14.7, 15.2, 15.8, 17.2, 18.5, 19.5, 20.5, 21.0, 22.0, 23.2, 25.0, 25.5, 26.3, 27.0, 27.5, 29.4, 30.5, 31.4, 32.2, 33.8, 34.9, 35.7, 37.7, 40.2 and 41.5°±0.2° 2θ.

Figure 20:
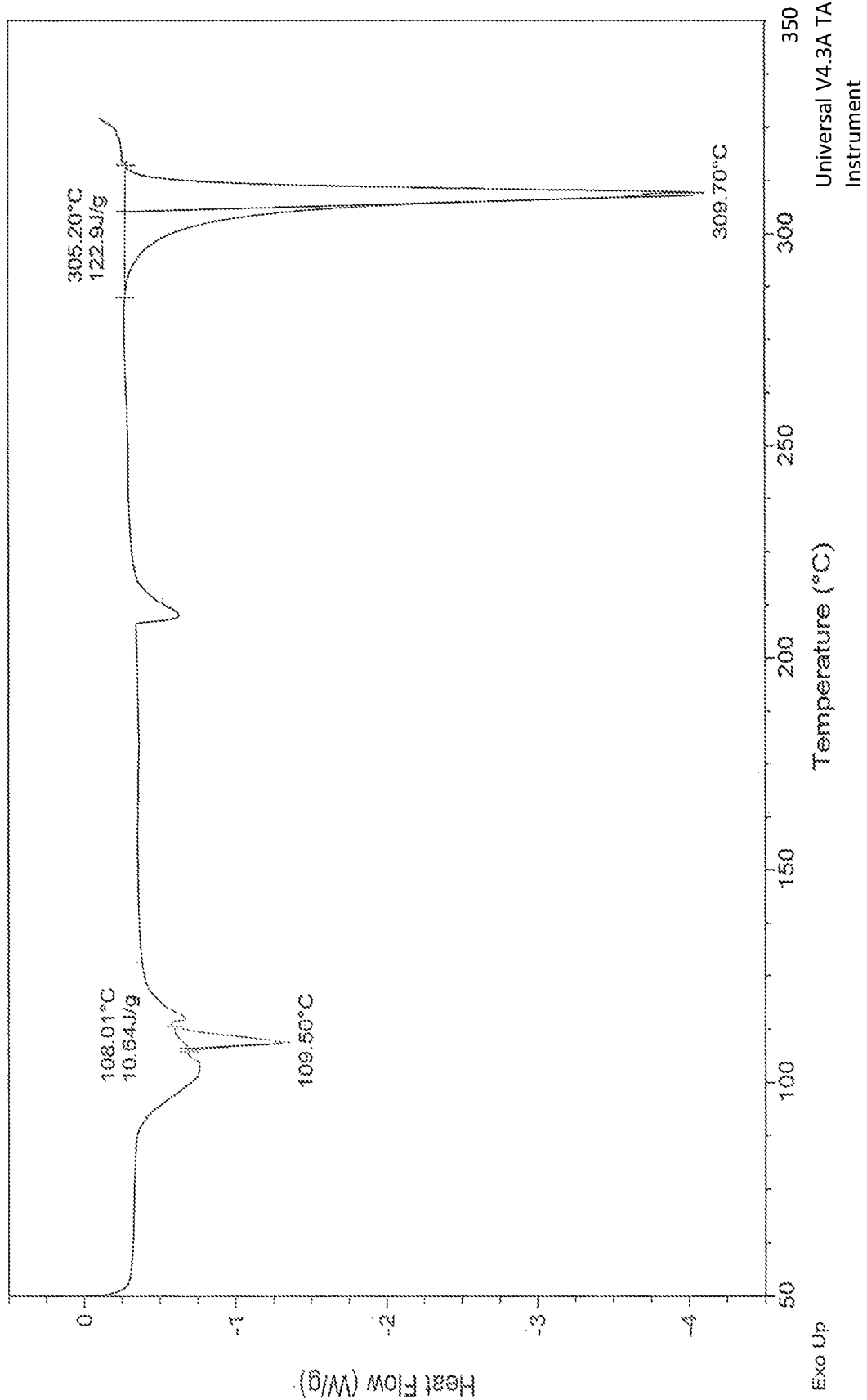
FIG. 20 is the characteristic differential scanning calorimetric (DSC) thermogram of Pazopanib hydrochloride Form-L9.

In another embodiment, the present invention provides pazopanib hydrochloride Form-L9 characterized by differential scanning calorimetry (DSC) substantially in accordance with FIG. 20.

Figure 21:
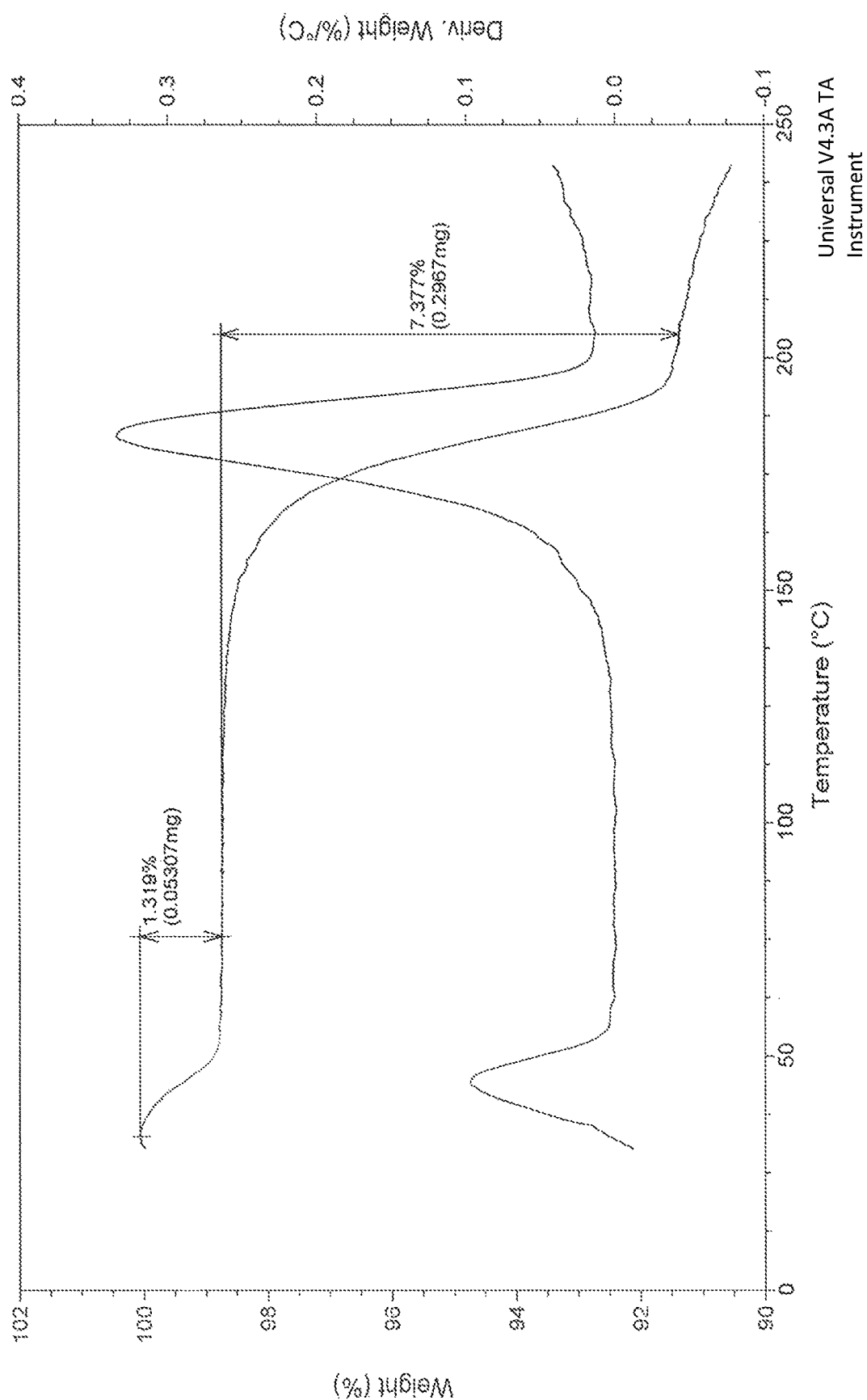
FIG. 21 is the characteristic thermo gravimetric analysis (TGA) of Pazopanib hydrochloride Form-L9.

In another embodiment, the present invention provides pazopanib hydrochloride Form-L9 characterized by thermo gravimetric analysis (TGA) substantially in accordance with FIG. 21.

In another embodiment, the present invention provides a process for preparation of pazopanib hydrochloride Form-L9, comprising:
 a) condensation of compound of Formula III and Formula C in tert-butanol in presence of catalytic amount of hydrochloric acid,
 b) heating the reaction mass to about reflux,
 c) stirring the step b) solution for about 2 to 6 hours,
 d) cooling the solution to precipitation, and
 e) isolating the pazopanib hydrochloride Form-L9.

The condensation of compound of Formula III and Formula C in presence of catalytic amount of hydrochloric acid is carried out at a temperature of about 25° C. to about reflux temperature; preferably at about 75° C. to about 85° C.

After completion of the reaction, the resultant reaction solution may be cooled at a temperature of about 25° C. to about 30° C. to precipitating pazopanib hydrochloride Form-L9. The pazopanib hydrochloride Form-L9 can be recovered by any conventional techniques known in the art, for example filtration.

In another embodiment, the present invention provides novel polymorphic Forms of N-(2-chloropyrimidin-4-yl)-N-2,3-trimethyl-2H-indazol-6-amine (Formula III); wherein the crystalline Forms are designated as Form-K1, Form-K2, Form-K3 and Form-K4.

In another embodiment, the present invention provides Formula III Form-K1.

Figure 22:
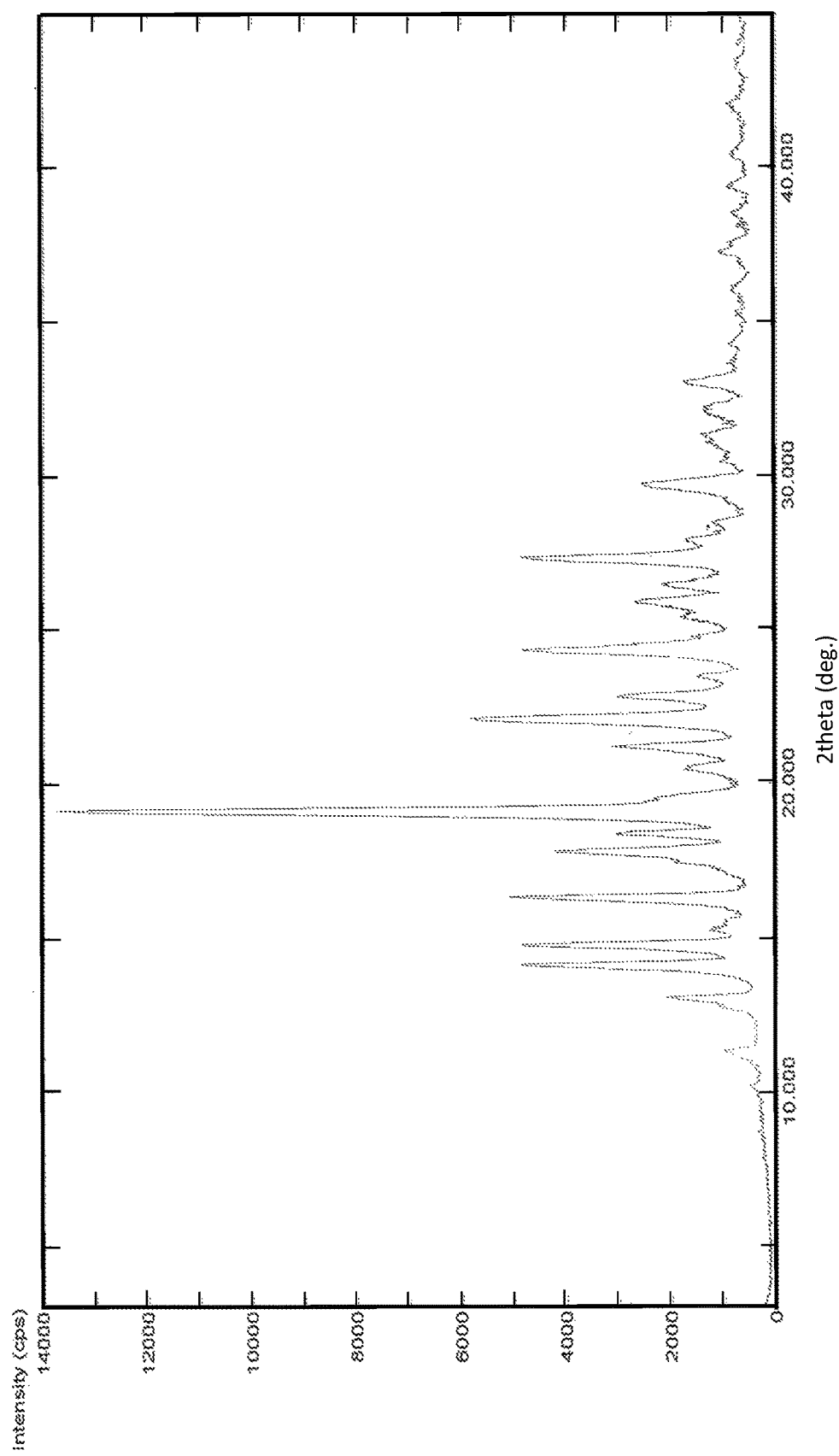
FIG. 22 is the characteristic powder X-ray diffraction (XRD) pattern of Formula III Form-K1.

In another embodiment, the present invention provides Formula III Form-K1 characterized by a powder X-Ray diffraction (PXRD) pattern substantially in accordance with FIG. 22.

In another embodiment, the present invention provides Formula III Form-K1 characterized by a PXRD pattern having peaks at about: 10.1, 11.3, 13.0, 14.1, 14.7, 15.2, 16.3, 17.7, 18.3, 19.1, 20.4, 21.2, 22.1, 22.8, 23.4, 24.3, 24.8, 25.3, 25.9, 26.5, 27.3, 27.8, 28.5, 29.6, 31.3, 32.1 and 33.0°±0.2° 2θ.

In another embodiment, the present invention provides a process for preparation of Formula III Form-K1, comprising:
 a) reacting a compound of Formula II with alkyl iodide in presence of potassium tert butoxide in dimethylformamide to obtain a compound of Formula III, and
 b) Isolating the Formula III Form-K1.

The starting material compound of Formula II is known in the art and can be prepared by any known method or obtained by the processes herein described in the present specification.

The reaction of compound of Formula II with alkyl iodide such as methyl iodide in presence of potassium tert butoxide in acetonitrile is carried out at a temperature of about 25° C. to about reflux temperature; preferably at about 25° C. to about 30° C.

After completion of the reaction, the resultant reaction solution can be isolated by conventional techniques known in the art such as isolated by quenching, solvent precipitation, crystallization, concentrated by subjecting the solution to heating and the like; preferably quenching the reaction mass in to water at a temperature 25° C. to about 30° C. The Formula III Form-K1 can be recovered by any conventional techniques known in the art, for example filtration.

In another embodiment, the present invention provides Formula III Form-K2.

Figure 23:
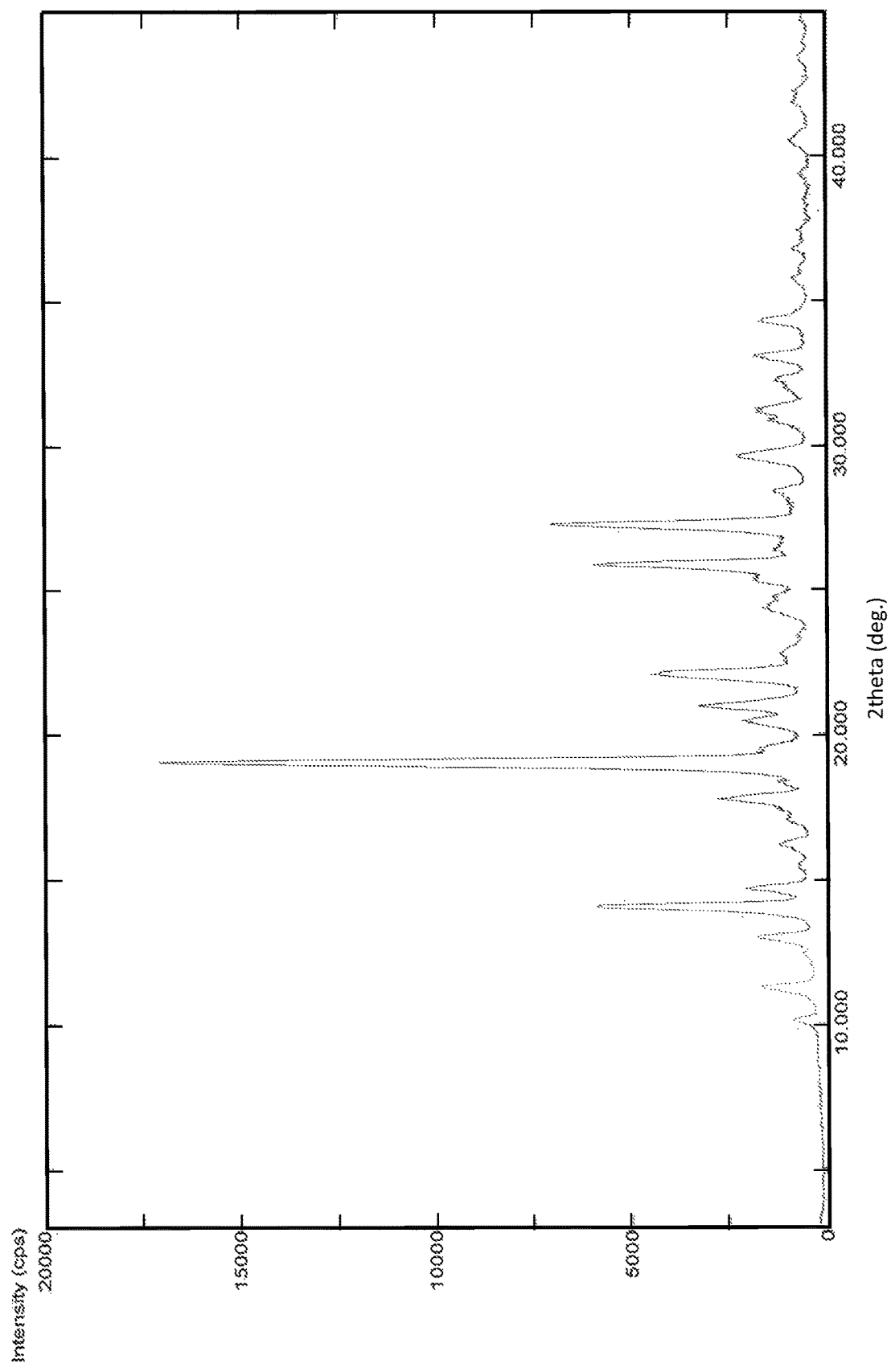
FIG. 23 is the characteristic powder X-ray diffraction (XRD) pattern of Formula III Form-K2.

In another embodiment, the present invention provides Formula III Form-K2 characterized by a powder X-Ray diffraction (PXRD) pattern substantially in accordance with FIG. 23.

In another embodiment, the present invention provides Formula III Form-K2 characterized by a PXRD pattern having peaks at about: 10.1, 11.2, 12.9, 14.0, 14.6, 16.1, 17.0, 17.7, 18.2, 19.0, 19.5, 20.4, 20.9, 22.1, 24.3, 24.7, 25.2, 25.8, 26.3, 27.2, 28.4, 29.6, 30.7, 31.2, 32.2, 33.1 and 34.2°±0.2° 2θ.

In another embodiment, the present invention provides a process for preparation of Formula III Form-K2, comprising:
 a) reacting a compound of Formula II with alkyl iodide in presence of potassium tert butoxide in tetrahydrofuran to obtain a compound of Formula III,
 b) concentrating the reaction mass to obtain a residue,
 c) adding water to the residue of step b); and
 d) isolating the Formula III Form-K2.

The starting material compound of Formula II is known in the art and can be prepared by any known method or obtained by the processes herein described in the present specification.

The reaction of compound of Formula II with alkyl iodide such as methyl iodide in presence of potassium tert butoxide in tetrahydrofuran is carried out at a temperature of about 25° C. to about reflux temperature; preferably at about 25° C. to about 30° C.

After completion of the reaction, the resultant reaction mass is concentrated under vacuum at a temperature of about 40° C. to about 45° C. to obtain a residue. To the obtained residue, water may be added to precipitate out the compound. The Formula III Form-K2 can be recovered by any conventional techniques known in the art, for example filtration.

In another embodiment, the present invention provides Formula III Form-K3.

Figure 24:
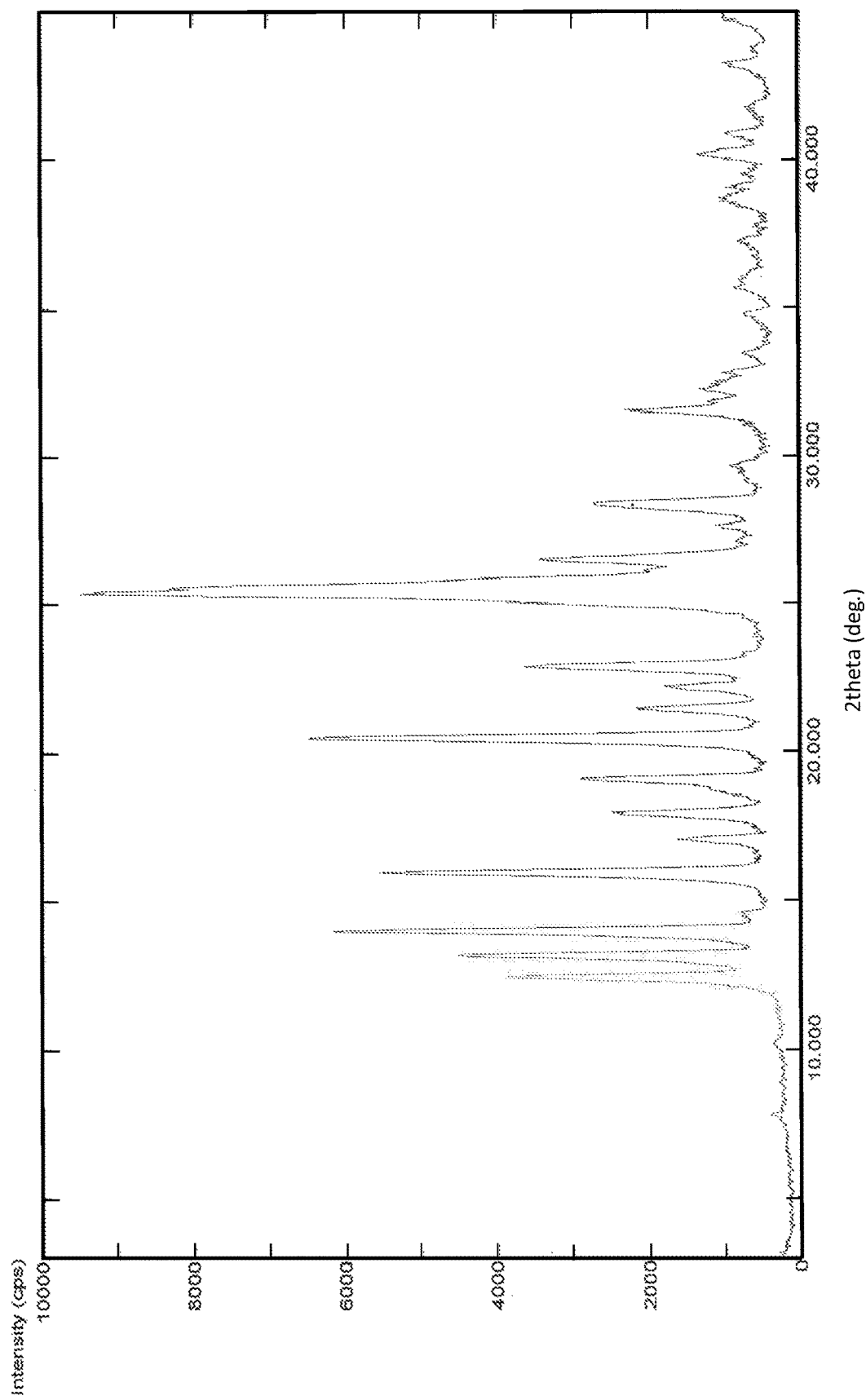
FIG. 24 is the characteristic powder X-ray diffraction (XRD) pattern of Formula III Form-K3.

In another embodiment, the present invention provides Formula III Form-K3 characterized by a powder X-Ray diffraction (PXRD) pattern substantially in accordance with FIG. 24.

In another embodiment, the present invention provides Formula III Form-K3 characterized by a PXRD pattern having peaks at about: 12.4, 13.1, 13.9, 14.5, 15.9, 17.0, 17.9, 19.1, 20.4, 21.4, 22.2, 22.9, 25.0, 25.3, 25.5, 26.1, 26.4, 27.5, 28.4, 29.7, 31.5, 31.8, 32.2, 32.8, 33.4, 34.7, 38.6, 39.0, 40.1, 40.8 and 43.1°±0.2° 2θ.

In another embodiment, the present invention provides a process for preparation of Formula III Form-K3, comprising:
 a) reacting a compound of Formula II with alkyl iodide in presence of potassium tert butoxide in acetonitrile to obtain a compound of Formula III, and
 b) isolating the Formula III Form-K3.

The starting material compound of Formula II is known in the art and can be prepared by any known method or obtained by the processes herein described in the present specification.

The reaction of compound of Formula II with alkyl iodide such as methyl iodide in presence of potassium tert butoxide in acetonitrile is carried out at a temperature of about 25° C. to about reflux temperature; preferably at about 25° C. to about 30° C.

After completion of the reaction, the resultant reaction solution can be isolated by conventional techniques known in the art such as isolated by quenching, solvent precipitation, crystallization, concentrated by subjecting the solution to heating and the like; preferably quenching the reaction mass in to water at a temperature 25° C. to about 30° C. The Formula III Form-K3 can be recovered by any conventional techniques known in the art, for example filtration.

In another embodiment, the present invention provides Formula III Form-K4.

Figure 25:
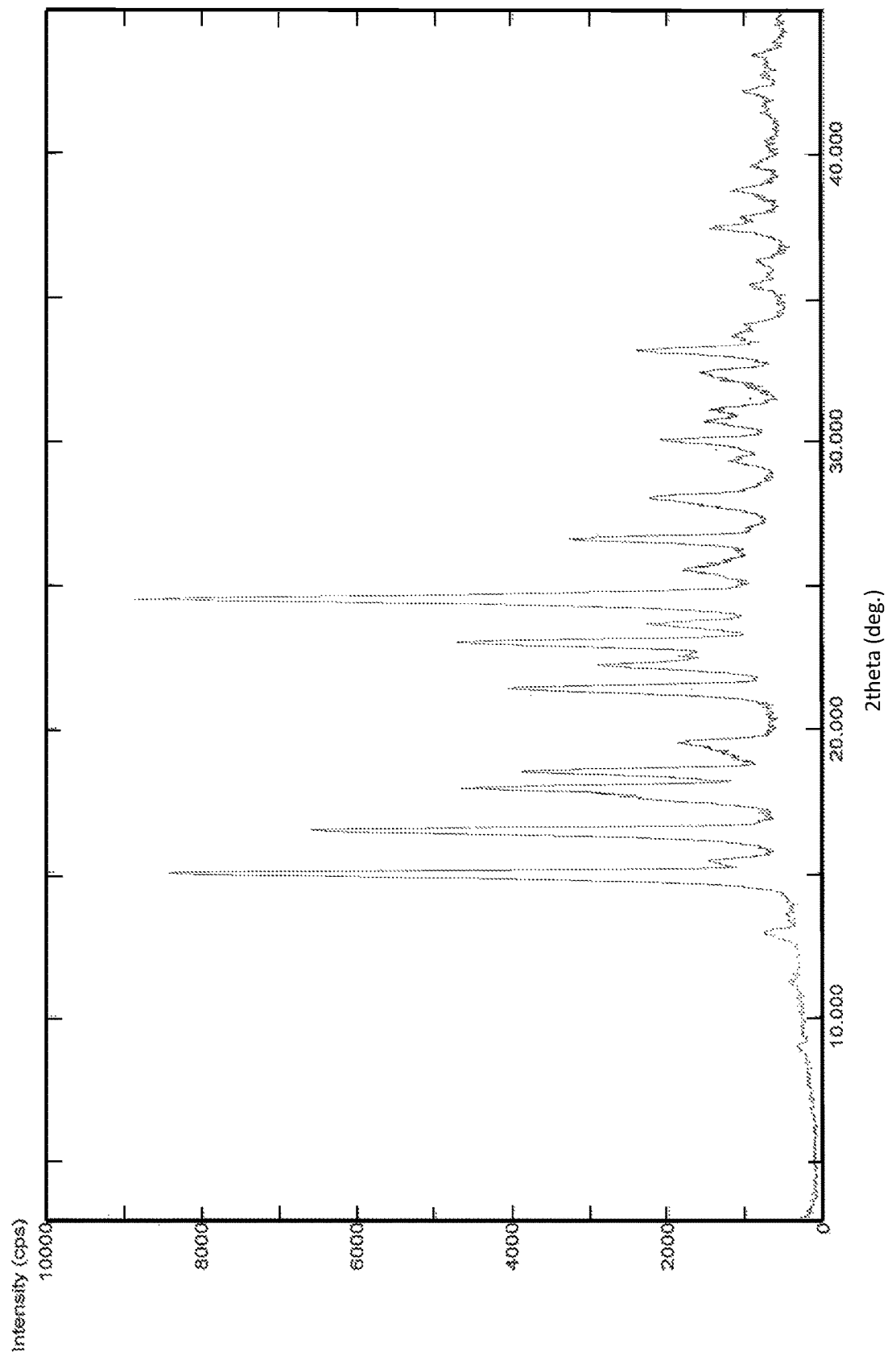
FIG. 25 is the characteristic powder X-ray diffraction (XRD) pattern of Formula III Form-K4.

In another embodiment, the present invention provides Formula III Form-K4 characterized by a powder X-Ray diffraction (PXRD) pattern substantially in accordance with FIG. 25.

In another embodiment, the present invention provides Formula III Form-K4 characterized by a PXRD pattern having peaks at about: 11.1, 12.9, 14.9, 15.4, 16.4, 17.9, 18.5, 19.4, 21.4, 22.2, 22.5, 23.0, 23.6, 24.5, 25.5, 26.5, 28.0, 29.3, 30.0, 30.7, 31.0, 32.2, 33.1, 33.7, 34.1, 35.4, 36.2, 37.4, 37.7, 38.7 and 39.5°±0.2° 2θ.

In another embodiment, the present invention provides a process for preparation of Formula III Form-K4, comprising:
 a) reacting compound of Formula II with alkyl iodide in presence of potassium tert butoxide in dimethylsulfoxide to obtain a compound of Formula III,
 b) concentrating the reaction mass to obtain a residue,
 c) adding water to the residue of step b); and
 d) isolating the Formula III Form-K4.

The starting material compound of Formula II is known in the art and can be prepared by any known method or obtained by the processes herein described in the present specification.

The reaction of compound of Formula II with alkyl iodide such as methyl iodide in presence of potassium tert butoxide in dimethylsulfoxide is carried out at a temperature of about 25° C. to about reflux temperature; preferably at about 25° C. to about 30° C.

After completion of the reaction, the resultant reaction mass is concentrated under vacuum at a temperature of about 40° C. to about 45° C. to obtain a residue. To the obtained residue, water may be added to precipitate out the compound. The Formula III Form-K4 can be recovered by any conventional techniques known in the art, for example filtration.

Figure 26:
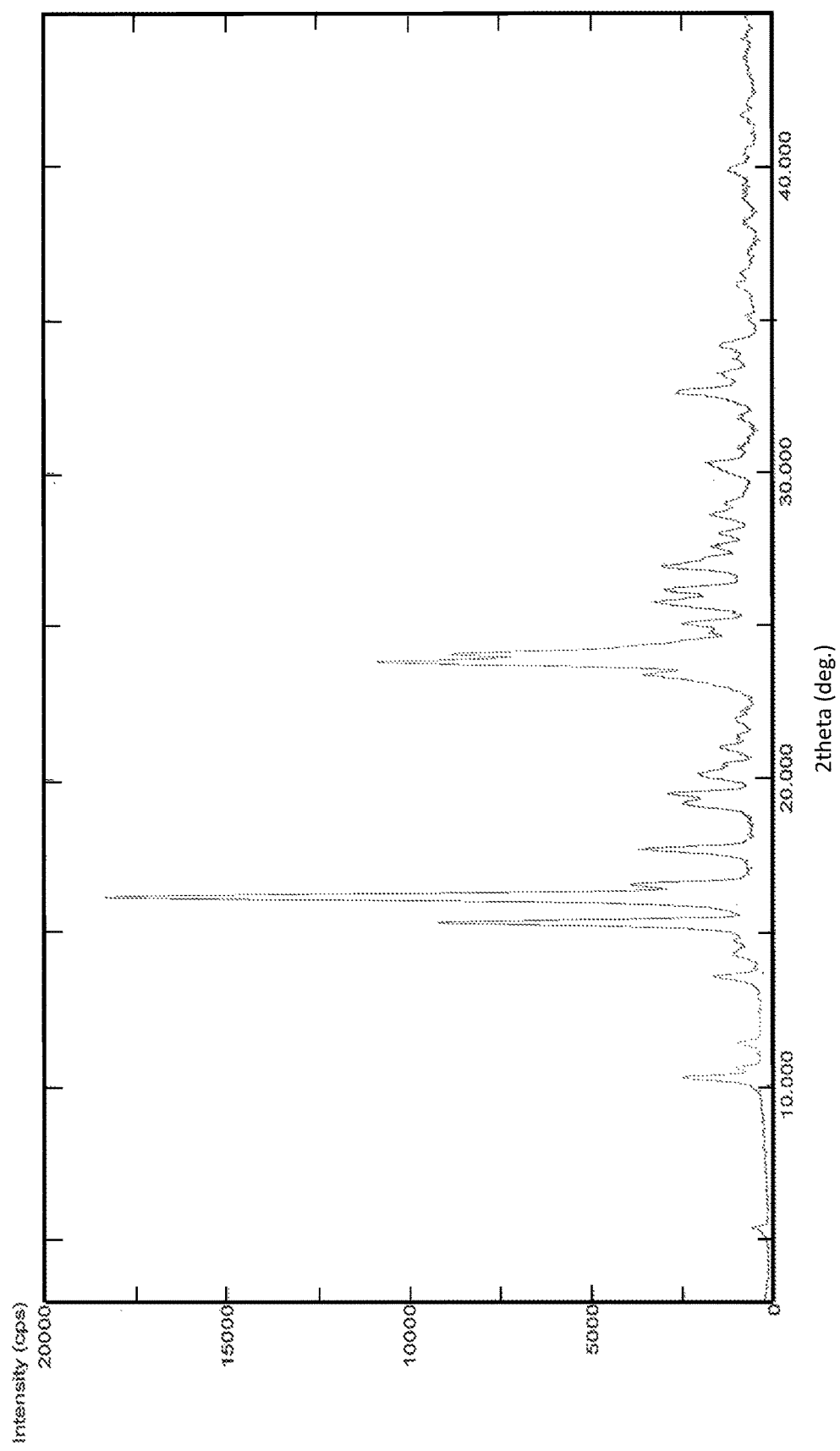
FIG. 26 is the characteristic powder X-ray diffraction (XRD) pattern of Pazopanib hydrochloride Form 1.

In another embodiment, the present invention provides pazopanib hydrochloride Form 1 characterized by a powder X-Ray diffraction (PXRD) pattern substantially in accordance with FIG. 26.

In another embodiment, the present invention provides pazopanib hydrochloride Form 1 characterized by a powder X-Ray diffraction (PXRD) pattern having peaks at about: 5.3, 10.2, 10.5, 11.4, 13.5, 14.2, 15.3, 16.1, 16.5, 17.7, 19.1, 19.5, 20.1, 20.4, 21.0, 21.9, 23.3, 23.8, 24.0, 25.0, 25.7, 26.1, 26.9, 27.6, 27.9, 28.6, 28.9, 30.3, 32.5, 33.2 and 34.1°±0.2° 2θ.

In another embodiment, the present invention provides a process preparation of pazopanib hydrochloride Form 1, comprising:
 a) providing a solution of pazopanib hydrochloride Form-L8 in methanol,
 b) partial evaporation of the solvent from the resultant solution,
 c) adding hydrochloric acid to the resultant reaction solution of step b); and
 d) isolating the pazopanib hydrochloride Form 1; wherein the pazopanib hydrochloride Form-L8 characterized by an XRPD pattern substantially in accordance with FIG. 16.

The step a) of providing a solution of pazopanib hydrochloride Form-L8 in methanol can be carried out at a temperature of about ambient to about reflux temperature; preferably, the solution is heated at about 55° C. to about 65° C.

The resultant reaction mass of step b) may be partially evaporated under vacuum at 50° C. to 55° C. followed by adding hydrochloric acid to the obtained solution to precipitating the pazopanib hydrochloride, which is then isolated by conventional techniques known in the art such as solvent precipitation, crystallization, concentrated by subjecting the solution to heating and the like; preferably cooling the reaction mass to a temperature of about 25° C. to about 30° C. The pazopanib hydrochloride Form 1 can be recovered by any conventional techniques known in the art, for example filtration.

In another embodiment, the present invention provides another process preparation of pazopanib hydrochloride Form 1, comprising:
 a) heating pazopanib hydrochloride Form-L8 up to a temperature of about 180° C.,
 b) cooling to room temperature, and
 c) recovering the pazopanib hydrochloride Form 1; wherein the pazopanib hydrochloride Form-L8 characterized by an XRPD pattern substantially in accordance with FIG. 16.

The step a) of heating the pazopanib hydrochloride Form-L8 can be carried out at a temperature of about 170° C. to 180° C. for a period of about 2 to 8 hours; preferably for a period of about 4 to 6 hours and then cooling the temperature to about room temperature and recovering the pazopanib hydrochloride Form 1 by methods known in the art.

In another embodiment, the present invention provides another process for preparation of pazopanib hydrochloride Form 1, comprising:
 a) condensation of compound of Formula III and Formula C in an alcohol solvent in presence of catalytic amount of hydrochloric acid,
 b) cooling the solution to precipitation, and
 c) isolating the pazopanib hydrochloride Form 1; where in the alcohol solvent is selected from the group consisting of n-propanol, n-butanol and 2-butanol.

The condensation of compound of Formula III and Formula C in presence of catalytic amount of hydrochloric acid is carried out at a temperature of about 25° C. to about reflux temperature for a period of about 10 hours to about 15 hours; preferably at reflux temperature for a period of about 12 hours.

After completion of the reaction, the resultant reaction solution can be isolated by conventional techniques known in the art such as isolated by crystallization, solvent precipitation, concentrated by subjecting the solution to heating, spray drying, freeze drying, evaporation on rotary evaporator under vacuum, agitated thin film evaporator (ATFE) and the like; preferably crystallization method by cooling the solution temperature to 25° C. to about 30° C. The pazopanib hydrochloride Form 1 can be recovered by any conventional techniques known in the art, for example filtration.

In another embodiment, the present invention provides novel polymorphic forms of pazopanib hydrochloride, having a chemical purity of 96% or more as measured by HPLC, preferably 99% or more, more preferably 99.5% or more.

In an embodiment, the present invention provides a pharmaceutical composition comprising pazopanib or a pharmaceutically acceptable salt and its polymorphic forms thereof, particularly pazopanib hydrochloride prepared by the processes of the present invention and at least one pharmaceutically acceptable excipient. Such pharmaceutical composition may be administered to a mammalian patient in any dosage form, e.g., liquid, tablet, powder, injectable solution, etc.

The present invention provides pazopanib hydrochloride and its intermediates, obtained by the above process, as analyzed using high performance liquid chromatography ("HPLC") with the conditions are tabulated below:

| | |
|---|---|
| Column | Zorbax bonus RP (150 × 4.6)mm, 3.5 um |
| Column/Sample temperature | 40° C./5° C. |
| Mobile phase | Mobile Phase-A: Buffer:Acetonitrile 95:5, (v/v) |
| | Mobile Phase-B: Acetonitrile:water 90:10, (v/v) |
| Buffer | 0.025M of sodium dihydrogen phosphate, pH adjusted with sodium hydroxide solution |
| Diluent | Water:Acetonitrile 40:60, (v/v) |
| Flow rate | 1.0 mL/min |
| Wavelength | 242 nm |
| Injection Volume | 10 μl |
| Elution | Gradient (T % B):0/20, 40/40, 50/60, 52/20 and 60/20 |

EXAMPLES

The present invention is further illustrated by the following examples, which are provided by way of illustration only and should not be construed to limit the scope of the invention.

Example 1

Preparation of N-(2-chloropyrimidin-4-yl)-2,3-dimethyl-2H-indazol-6-amine of Formula II To a 3 L round bottom flask fitted with a mechanical stirrer, thermometer socket was charged dimethylsulfoxide (250 ml), 2,3-di methyl-2H-indazol-6-amine of Formula A (50 gms, 0.3092 moles), triethylamine (37.5 gms, 0.3710 moles) and stirred for 10 min at 25-30° C. Charged 2,4-dichloropyrimidine of Formula B (55.3 gms, 0.3710 moles) and allowed to stir for 12 hrs at 25-30° C. After completion of the reaction to the reaction mass charged water (1500 ml), adjusted the reaction mass pH to 7-7.5 with 10% HCl and allowed to stir for 1 hrs at 25-30° C. Filtered and washed with water (250 ml). To the obtained wet material was charged acetonitrile (250 ml) and stirred for 1 hrs at 25-30° C. Filtered and washed with acetonitrile (50 ml). To the obtained wet material was charged acetonitrile (100 ml) and stirred for 2 hrs at 80-85° C. Cooled the reaction mass temperature to 25° C., filtered the solids and washed with acetonitrile (100 ml), dried under vacuum at 40-45° C. for 4 hrs to obtain title compound.

Yield: 70 gms
Purity by HPLC: 99.5%
Impurity 1: 0.01%; Impurity 5: 0.3%

Example-2

Preparation of N-(2-chloropyrimidin-4-yl)-2,3-dimethyl-2H-indazol-6-amine of Formula II To a 250 ml round bottom flask fitted with a mechanical stirrer, thermometer socket was charged 2,3-dimethyl-2H-indazol-6-amine of Formula A (10 gms), triethylamine (7.5 gms) in water (100 ml). Charged 2,4-dichloropyrimidine of Formula A (11.1 gms) at 40-45° C. and allowed to stir for 10 hrs. After completion of the reaction, pH of the reaction mixture was adjusted to 7.5-8.0 with aq hydrochloride solution and allowed to stir for 2 hrs. The obtained solids were filtered and washed with water and acetonitrile to obtain title compound.

Yield: 13 gms
Purity by HPLC: 99.2%
Impurity 1: Not detected, Impurity 5: 0.36%

Example 3

Preparation of N-(2-chloropyrimidin-4-yl)-N,2,3-trimethyl-2H-indazol-6-amine of Formula III To a 2 L round bottom flask fitted with a mechanical stirrer, thermometer socket, addition funnel was charged acetone (380 ml), sodiumhydroxide solution (dissolved 8.8 gms, 0.2191 moles of sodiumhydroxide flakes in 10 ml water) and allowed to stir for 15 min at 25-30° C. Charged N-(2-chloropyrimidin-4-yl)-2,3-dimethyl-2H-indazol-6-amine of Formula II (40 gms, 0.1461 moles), added methyl iodide (27 gms, 0.19 moles of methyl iodide was dissolved in 20 ml of acetone) in 30-45 min at 25-30° C., stirred for 2 hrs at same temperature. After completion of the reaction pH of the reaction mass was adjusted to 7.0-7.5 with 10% HCl. Distilled off solvent completely under vacuum at 40-45° C. The obtained residue was cooled to 30° C. and charged water (400 ml), pH of the aqueous layer was adjusted to 7.0-7.5 with 10% HCl and stirred for 2 hrs at 25-30° C. The obtained solids were filtered and washed with water (200 ml), dried under vacuum at 45-50° C. for 4 hrs to obtain title compound. The obtained compound was optionally purified by chagrining the crude compound in ethylacetate (520 ml) and heated to reflux for complete dissolution, after 1 hrs cool the reaction mass temperature to 60° C., charged carbon and refluxed or 1 hrs. Filtered the reaction mass through celite bed and washed with ethylacetate (80 ml), cooled the reaction mass temperature to 25-30° C. and stirred for 1 hrs. Again gradually cool the reaction mass temperature to 0-5° C. and allowed to stir for 3 hrs. The obtained solids were filtered and washed with ethyl acetate (80 ml), dried under vacuum at 45-50° C. for 4 hrs to obtain title compound.

Yield: 32 gms
Purity by HPLC: 99.4%
Impurity 2: Not detected, Impurity 3: Not detected & Impurity 4: Not detected,
Impurity 6: 0.34%

Example 4

Preparation of N-(2-chloropyrimidin-4-yl)-N,2,3-trimethyl-2H-indazol-6-amine of Formula III To a 500 ml round bottom flask fitted with a mechanical stirrer, thermometer socket was charged acetone (100 ml), N-(2-chloropyrimidin-4-yl)-2,3-dimethyl-2H-indazol-6-amine of Formula II (10 gms), sodium hydroxide solution (dissolved 2.2 gms sodiumhydroxide flakes in 2.2 ml water). To the reaction mixture was charged dimethyl sulfate (7.8 gms) at room temperature and allowed to stir for 2 hrs. After completion of the reaction, solvent was removed under vacuum at 40-45° C., to the obtained residue was added water. The obtained solids were filtered and dried under vacuum at 40-45° C.' to obtain title compound as a cream color solid.

Yield: 9 gms
Purity by HPLC: 99.4%
Impurity 2: not detected, Impurity 3: Not detected & impurity 4: Not detected;
Impurity 6: 0.24%

Example 5

Preparation of Pazopanib Hydrochloride

To a 2 L round bottom flask fitted with a mechanical stirrer, thermometer socket was charged methanol (520 ml), N-(2-chloropyrimidin-4-yl)-N,2,3-trimethyl-2H-indazol-6-amine of Formula III (40 gms, 0.1390 moles), 5-amino-2-methyl benzenesulfonamide of Formula C (29.3 gms, 0.1571 moles) at 25-30° C. Reaction mass temperature was raised to reflux to get clear solution. To the reaction mass charged catalytic amount of HCl (0.04 ml) at 55-60° C. and allowed to stir for 8 hrs. After completion of the reaction, temperature allowed to cool 25-30° C. and stirred for 1 hrs. The reaction mass temperature was allowed to cool 0-5° C. and stirred for 2 hrs. Solids were filtered and washed with chilled methanol (80 ml), dried under vacuum at 45-50° C. for 4 hrs to obtain title compound.

Yield: 60 gms
Purity by HPLC: 99%
Impurity 1: Not detected; Impurity 2: Not detected; Impurity 3: 0.05%; Impurity 4: 0.05%; Impurity 5: Not detected; Impurity 6: Not detected; Formula-III: 0.7%; Formula C: 0.2%

Example 6

Preparation of Pazopanib Hydrochloride

To a 250 ml round bottom flask fitted with a mechanical stirrer, thermometer socket was charged tetrahydrofuran (130 ml), N-(2-chloropyrimidin-4-yl)-N,2,3-trimethyl-2H-indazol-6-amine of Formula III (10 gms, 0.1390 moles), 5-amino-2-methyl benzenesulfonamide of Formula C (7.32 gms, 0.039 moles) and 4 drops of concentrated hydrochloride at 25-30° C. Reaction mass temperature was raised to reflux for 10-12 hrs. After completion of reaction, temperature of the reaction mass was cooled to room temperature and filtered the obtained solids and washed with tetrahydrofuran to obtain title compound as an off white solid.

Yield: 13.1 gms
Purity by HPLC: 99.3%
Formula III: 0.07%; Formula C: 0.07%

Example 7

Preparation of Pazopanib Hydrochloride

To a 250 ml round bottom flask fitted with a mechanical stirrer, thermometer socket was charged acetonitrile (130 ml), N-(2-chloropyrimidin-4-yl)-N,2,3-trimethyl-2H-indazol-6-amine of Formula III (10 gms, 0.035 moles), 5-amino-2-methyl benzenesulfonamide of Formula C (7.32 gms, 0.039 moles) and 4 drops of concentrated hydrochloride at 25-30° C. Reaction mass temperature was raised to reflux for 10-12 hrs. After completion of reaction, temperature of the reaction mass was cooled to room temperature and filtered the obtained solids and washed with acetonitrile to obtain title compound as an off white solid.

Yield: 13.1 gms
Purity by HPLC: 99.4%
Formula III: 0.09%; Formula C: 0.05%

Example 8

Purification of Pazopanib Hydrochloride

To a 10 L round bottom flask fitted with a mechanical stirrer, thermometer socket was charged methanol (4.8 lit), Pazopanib hydrochloride from example-5 (60 gms) at 25-30° C. Reaction mass temperature was allowed to raise 65° C. and stirred for 2 hrs to get clear solution. To the clear solution was given carbon treatment and filtered the reaction mass at hot condition (55° C.-65° C.) and washed with methanol (180 ml), distilled off methanol under atmospheric pressure at 60-65° C. upto reaction mass volume 45 v remain. Charged seed of pazopanib hydrochloride to the reaction mass at 60° C. and followed by distilled off methanol under atmospheric pressure at 60-65° C. upto reaction mass volume 20 v remain, reaction mass temperature was allowed to cool 25°-29° C. and stirred for 2 hrs. The obtained solids were filtered and washed with methanol (120 ml), dried under vacuum at 40-45° C. for 4 hrs to obtain title compound.

Yield: 54 gms
Purity by HPLC: 99.9%
Impurity 1: 0%; Impurity 2: 0%; Impurity 3: 0.03%; Impurity 4: 0.01%; Impurity 5: 0; Impurity 6: 0; Formula-III: 0.001%; Formula C: 0.05%
The XRPD is set forth in FIG. 26
DSC: 311° C.

Example 9

Purification of Pazopanib Hydrochloride
To a 3 L round bottom flask fitted with a mechanical stirrer, thermometer socket was charged methanol (2 lit), Pazopanib hydrochloride (25 gms) at 25-30° C. Reaction mass temperature was allowed to raise 65° C.' and stirred for 2 hrs to get clear solution. Filtered the reaction mass and washed with methanol (125 ml), distilled off methanol at 60-65° C. upto reaction mass volume 25 v remain. Charged catalytic amount of HCl (0.02 ml) at 55-60° C., reaction mass temperature was allowed to cool 25-30° C. and stirred for 2 hrs. Reaction mass temperature was further cooled to 0-5° C. and allowed to stir for 2 hrs. The obtained solids were filtered and washed with chilled methanol (50 ml), dried under vacuum at 40-45° C. for 4 hrs to obtain title compound.

Yield: 20 gms
Purity by HPLC: 99.5%
Formula-III: 0.01%

Example 10

Preparation of Pazopanib Hydrochloride Form-L1

Pazopanib hydrochloride (1 g) was dissolved in methanol (60 ml) at 25-30° C. and heated to about 60-65° C. The reaction mass was stirred for 2 hours at same temperature to get a clear solution. The resultant solution was filtered and cooled to room temperature. In another RBF methanol (10 ml) was taken and cooled to −15° C., added the above obtained filtered to the chilled methanol at −15° C.; to −10° C. The obtained solid was filtered, washed with methanol (5 ml), suck dried and dried under vacuum at 40-45° C. for 4 hr to yield pazopanib hydrochloride Form-L1.

Yield: 0.76 g
HPLC purity: 99.99%
Moisture content—7.37% w/w
The XRPD is set forth in FIG. 1
The DSC is set forth in FIG. 2
The TGA is set forth in FIG. 3

Example 11

Preparation of Pazopanib Hydrochloride Form-L1

Pazopanib hydrochloride (1 g) was dissolved in dichloromethane and methanol mixture (1:1, 35 ml) at about 60-65° C. The reaction mass was stirred for 2 hrs at same temperature to get a clear solution. The resultant solution was allowed to cool to −15° C. and stirred for 2-3 hours at same temperature. The obtained solid was filtered, washed with methanol (5 ml), suck dried and dried under vacuum at 40-45° C. for 4 h to yield pazopanib hydrochloride Form-L1.

Yield: 0.16 g
HPLC purity: 99.97%
Moisture content—7.42% w/w
The XRPD is set forth in FIG. 1

Example 12

Preparation of Pazopanib Hydrochloride Form-L2

Pazopanib hydrochloride (1 g) was dissolved in methanol (60 ml) at about 60-65° C. The reaction mass was stirred for 2 hours at same temperature to get a clear solution. The reaction mass was filtered and cooled to room temperature. The resultant filterate was allowed to cool to 0-5° C. and stirred for 2-3 hours at same temperature. The obtained solid was filtered, washed with methanol (5 ml), suck dried and dried under vacuum at 40-45° C. for 4 h to yield pazopanib hydrochloride Form-L2.

Yield: 0.6 g
HPLC purity: 99.95%
The XRPD is set forth in FIG. 4

Example 13

Preparation of Pazopanib Hydrochloride Form-L3

Pazopanib hydrochloride (1 g) was dissolved water (300 ml) at about 95-100° C. The reaction mass was stirred for 2 hrs at same temperature to get a clear solution. The resultant solution was allowed to cool to 25-30° C. and stirred for 2-3 hours at same temperature. The obtained solid was filtered, washed with water (5 ml), suck dried and dried under vacuum at 40-45° C. for 4 h to yield pazopanib hydrochloride Form-L3.

Yield: 0.38 g
HPLC purity: 99.80%
The XRPD is set forth in FIG. 5
The DSC is set forth in FIG. 6

Example 14

Preparation of Pazopanib Hydrochloride Form-L4

Pazopanib hydrochloride (1 g) was dissolved in ethanol (400 ml) at about 75-80° C. The reaction mass was stirred for 2 hours at same temperature to get a clear solution. The resultant solution was filtered and cooled to room temperature. In another RBF ethanol (10 ml) was taken and cooled to −15° C., added the above obtained filterate to the chilled ethanol at −15° C. to −10° C. The obtained solid was filtered, washed with ethanol (5 ml), suck dried and dried under vacuum at 40-45° C. for 4 h to yield pazopanib hydrochloride Form-L4.

Yield: 0.5 g
HPLC purity: 99.97%
Moisture content—1.68% w/w
The XRPD is set forth in FIG. 7
The TGA is set forth in FIG. 8

Example 15

Preparation of Pazopanib Hydrochloride Form-L5

Pazopanib hydrochloride (1 g) was dissolved in n-propanol (400 ml) at about 95-100° C. The reaction mass was stirred for 2 hours at same temperature to get a clear solution. The resultant solution was filtered and cooled to room temperature. In another RBF n-propanol (10 ml) was taken and cooled to −15° C., added the above obtained filterate to the chilled n-propanol at −15° C. to −10° C. The obtained solid was filtered, washed with n-propanol (5 ml), suck dried and dried under vacuum at 40-45° C. for 4 h to yield pazopanib hydrochloride Form-L5.

Yield: 0.6 g
HPLC purity: 99.96%
Moisture content—2.39% w/w
The XRPD is set forth in FIG. 9
The DSC is set forth in FIG. 10
The TGA is set forth in FIG. 11

Example 16

Preparation of Pazopanib Hydrochloride Form-L6

Pazopanib hydrochloride (1 g) was dissolved in n-butanol (400 ml) at about 115-120° C. The reaction mass was stirred for 2 hours at same temperature to get a clear solution. The resultant solution was filtered and cooled to room temperature. In another RBF n-butanol (10 ml) was taken and cooled to −1.5° C., added the above obtained filterate to the chilled n-butanol at −15° C. to −10° C. The obtained solid was filtered, washed with n-butanol (5 ml), suck dried and dried under vacuum at 40-45° C. for 4 h to yield pazopanib hydrochloride Form-L6.

Yield: 0.8 g
HPLC purity: 99.99%
Moisture content—8.01% w/w
The XRPD is set forth in FIG. 12
The DSC is set forth in FIG. 13
The TGA is set forth in FIG. 14

Example 17

Preparation of Pazopanib Hydrochloride Form-L7

Pazopanib hydrochloride (1 g) was dissolved in 2-butanol (400 ml) at about 95-100° C. The reaction mass was stirred for 2 hours at same temperature to get a clear solution. The resultant solution was filtered and cooled to room temperature. In another RBF 2-butanol (10 v) was taken and cooled to −15° C., added the above obtained filterate to the chilled 2-butanol at −15° C. to −10° C. The obtained solid was filtered, washed with 2-butanol (5 ml), suck dried and dried under vacuum at 40-45° C. for 4 h to yield pazopanib hydrochloride Form-L7.

Yield: 0.25 g
HPLC purity: 99.73%
The XRPD is set forth in FIG. 15

Example 18

Preparation of Pazopanib Hydrochloride Form-8

To a solution of Formula III (3.0 g) and 5-amino-2-methyl benzene sulfonamide of Formula C (2.2 g) in tert-butanol (45 ml) was added four drops of concentrated hydrochloric acid. The mixture was heated to 80-85° C. for 10-12 hours. The reaction mass temperature was cooled to 25-30° C. The obtained solids were filtered and washed with tert-butanol (1 ml), suck dried and dried under vacuum at 40-45° C. for 4 h to yield pazopanib hydrochloride Form-L8.

Yield: 4.5 g
HPLC purity: 98.94%
The XRPD is set forth in FIG. 16
The DSC is set forth in FIG. 17
The TGA is set forth in FIG. 18

Example 19

Preparation of Pazopanib Hydrochloride Form-L9

To a solution of Formula III (3.0 g) and 5-amino-2-methyl benzene sulfonamide of Formula C (2.2 g) in tert-butanol (45 ml) was added four drops of concentrated hydrochloric acid. The mixture was heated to 80-85° C. for 4-5 hours. The reaction mass temperature was cooled to 25-30° C. The obtained solids were filtered and washed with tert-butanol (1 ml), suck dried and dried under vacuum at 40-45° C. for 4 h to yield pazopanib hydrochloride Form-L8.

Yield: 3.6 g
HPLC purity: 98.19%
The XRPD is set forth in FIG. 19
The DSC is set forth in FIG. 20
The TGA is set forth in FIG. 21

Example 20

Preparation of Form-K1 of Formula III

To a solution of N-(2-chloropyrimidin-4-yl)-2,3-dimethyl-2H-indazol-6-amine (1.0 g) of Formula II in dimethyl formamide (10 ml) was added potassium tert butoxide (0.62 g) and methyl iodide (0.78 g) 25-35° C. The reaction mixture was stirred for 12 hours at 25-35° C. Quenched the above reaction mass in to water and the precipitate was collected by filtration and wash with water (2 ml) and the wet material was dried at 40-45° C. to afford Form-K1 of Formula III.

Yield: 0.7 g
HPLC purity: 97.11%
The XRPD is set forth in FIG. 22

Example 21

Preparation of Form-K2 of Formula III

To a solution of N-(2-chloropyrimidin-4-yl)-2,3-dimethyl-2H-indazol-6-amine (1.0 g) of Formula II in tetrahydrofuran (100 ml) was added potassium tert butoxide (0.62 g) and methyl iodide (0.78 g) 25-35° C. The reaction mixture was stirred for 12 hours at 25-35° C. The resultant solution was completely evaporated under vacuum at 40-45° C. To the obtained residue was added water (10 ml) and solids were filtered and washed with water (2 ml) and the wet material was dried at 40-45° C. to afford Form-K2 of Formula III.

Yield: 1.0 g
HPLC purity: 99.72%
The XRPD is set forth in FIG. 23

Example 22

Preparation of Form-K3 of Formula III

To a solution of N-(2-chloropyrimidin-4-yl)-2,3-dimethyl-2H-indazol-6-amine (1.0 g) of Formula II in acetonitrile (100 ml) was added potassium tert butoxide (0.62 g) and methyl iodide (0.78 g) 25-35° C. The reaction mixture was stirred for 12 hours at 25-35° C. Quenched the above reaction mass in to water and the precipitate was collected by filtration and wash with water (2 ml) and the wet material was dried at 40-45° C. to afford Form-K3 of Formula III Yield: 1.0 g.
HPLC purity: 99.61%
The XRPD is set forth in FIG. 24

Example 23

Preparation of Form-K4 of Formula III

To a solution of N-(2-chloropyrimidin-4-yl)-2,3-dimethyl-2H-indazol-6-amine (1.0 g) of Formula II in dimethylsulfoxide (100 ml) was added potassium tert butoxide (0.62 g) and methyl iodide (0.78 g) 25-35° C. The reaction mixture was stirred for 12 hours at 25-35° C. The resultant solution was completely evaporated under vacuum at 40-45° C. To the obtained residue was added water (10 ml) and solids were filtered and washed with water (2 ml) and the wet material was dried at 40-45° C. to afford Form-K4 of Formula III.

Yield: 1.0 g
HPLC purity: 95.97%
The XRPD is set forth in FIG. 25

Example 24

Preparation of Pazopanib Hydrochloride Form 1

Pazopanib hydrochloride Form-L8 (20 g) was dissolved in methanol (1600 ml) at about 60-65° C. The reaction mass was stirred for 2 hours at same temperature to get a clear solution. The solution was partly evaporated under vacuum at −50-55° C. up to 50 vol remains in the flask. To the resultant solution added catalytic amount of hydrochloric acid at 50-55° C., cooled the reaction mass temperature to 25-30° C. and allowed to stir for 2-3 hours. The solids were filtered and washed with methanol (100 ml) to obtain Pazopanib hydrochloride Form 1.

Yield: 13.0 g
HPLC purity: 99.42%
The XRPD is set forth in FIG. 26

Example 25

Preparation of Pazopanib Hydrochloride Form 1

Pazopanib hydrochloride Form-L8 (1 g) was placed on a petri dish heated the compound to 170° C. and maintained at 170-180° C. for 4 hours. Then the reaction mass temperature was allowed to cool to 25-30° C. to obtain Pazopanib hydrochloride Form 1.

Yield: 0.9 g
HPLC purity: 99.75%
The XRPD is set forth in FIG. 26

Example 26

Preparation of Pazopanib Hydrochloride Form 1

To a solution of Formula III (5 g) and 5-amino-2-methyl benzene sulfonamide of Formula C (3.7 g) in n-propanol (25 ml) was added four drops of concentrated hydrochloric acid. The mixture was heated to 95-100° C. for 10-12 hours. The reaction mass temperature was slowly cooled to 0-5° C., The obtained solids were filtered and washed with n-propanol (10 ml), suck dried and dried under vacuum at 40-45° C. for 4 h to yield Pazopanib hydrochloride Form 1.

Yield: 7.2 g
HPLC purity: 99.05%
The XRPD is set forth in FIG. 26

Example 27

Preparation of Pazopanib Hydrochloride Form 1

To a solution of Formula III (5 g) and 5-amino-2-methyl benzene sulfonamide of Formula C (3.7 g) in n-butanol (25 ml) was added four drops of concentrated hydrochloric acid. The mixture was heated to 115-120° C. for 10-12 hours. The reaction mass temperature was cooled to 25-35° C. The obtained solids were filtered and washed with n-butanol (7.4 ml), suck dried and dried under vacuum at 40-45° C. for 4 h to yield pazopanib hydrochloride Form 1.

Yield: 7.1 g
HPLC purity: 98.48%
The XRPD is set forth in FIG. 26

Example 28

Preparation of Pazopanib Hydrochloride Form 1

To a solution of Formula III (5 g) and 5-amino-2-methyl benzene sulfonamide of Formula C (3.7 g) in 2-butanol (2.5 ml) was added four drops of concentrated hydrochloric acid. The mixture was heated to 95-100° C. for 10-12 hours. The reaction mass temperature was cooled to 25-35° C. The obtained solids were filtered and washed with 2-butanol (10 ml), suck dried and dried under vacuum at 40-45° C. for 4 h to yield pazopanib hydrochloride Form 1.

Yield: 7.7 g
HPLC purity: 94.1%
The XRPD is set forth in FIG. 26

While the invention has been described with reference to above detailed description and the preferred examples, it is not intended to be limited thereto. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the specification appended hereto.

We claim:

1. Crystalline Form-K1 of N-(2-chloropyrimidin-4-yl)-N-2,3-trimethyl-2H-indazol-6-amine, characterized by a powder X-Ray diffraction (PXRD) pattern substantially in accordance with FIG. 22.

2. A process for preparation of N-(2-chloropyrimidin-4-yl)-N-2,3-trimethyl-2H-indazol-6-amine Form-K1 characterized by a powder X-Ray diffraction (PXRD) pattern according to FIG. 22, comprising:
   a) reacting a compound of Formula II with methyl iodide in presence of potassium tert butoxide in dimethylformamide to obtain a compound of Formula III Form-K1,

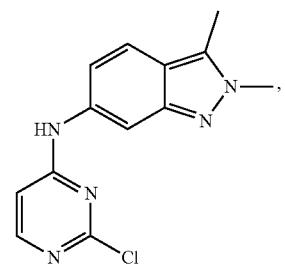

Formula II

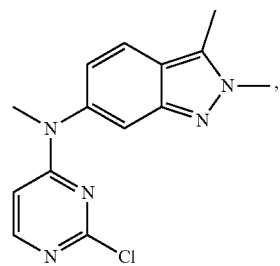

Formula III and
   b) isolating the Formula III Form-K1.

3. The process of claim 2, wherein the step a) is carried out at a temperature of about 25° C. to about reflux temperature.

4. Crystalline Form-K2 of N-(2-chloropyrimidin-4-yl)-N-2,3-trimethyl-2H-indazol-6-amine, characterized by a powder X-Ray diffraction (PXRD) pattern substantially in accordance with FIG. 23.

5. A process for preparation of N-(2-chloropyrimidin-4-yl)-N-2,3-trimethyl-2H-indazol-6-amine Form-K2 characterized by a powder X-Ray diffraction (PXRD) pattern according to FIG. 23, comprising:
   a) reacting a compound of Formula II with methyl iodide in presence of potassium tert butoxide in tetrahydrofuran to obtain a compound of Formula III,

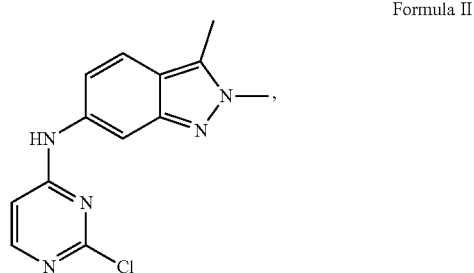

Formula II

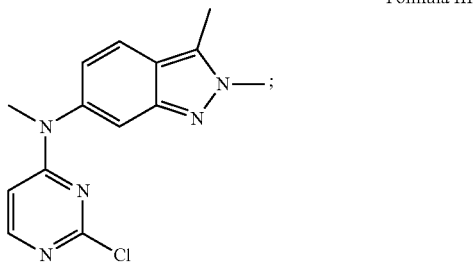

Formula III b) concentrating the reaction mass to obtain a residue;
   c) adding water to the residue of step b); and
   d) isolating the Formula III Form-K2.

6. The process of claim 5, wherein the step a) is carried out at a temperature of about 25° C. to about reflux temperature.

7. The process of claim 5, wherein the step b) is carried out by removing the solvent under vacuum at 40° C. to about 45° C.

8. Crystalline Form-K3 of N-(2-chloropyrimidin-4-yl)-N-2,3-trimethyl-2H-indazol-6-amine, characterized by a powder X-Ray diffraction (PXRD) pattern substantially in accordance with FIG. 24.

9. A process for preparation of N-(2-chloropyrimidin-4-yl)-N-2,3-trimethyl-2H-indazol-6-amine Form-K3 characterized by a powder X-Ray diffraction (PXRD) pattern according to FIG. 24, comprising:
   a) reacting a compound of Formula II with methyl iodide in presence of potassium tert butoxide in acetonitrile to obtain a compound of Formula III, Formula II

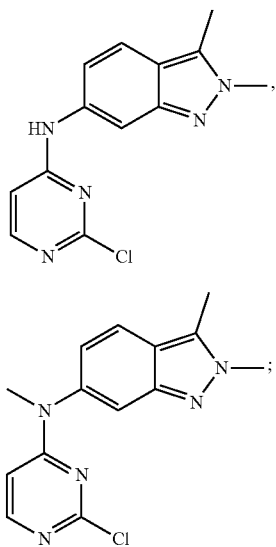

Formula III and b) isolating the Formula III Form-K3.

10. The process of claim 9, wherein the step a) is carried out at a temperature of about 25° C. to about reflux temperature.

11. Crystalline Form-K4 of N-(2-chloropyrimidin-4-yl)-N-2,3-trimethyl-2H-indazol-6-amine, characterized by a powder X-Ray diffraction (PXRD) pattern substantially in accordance with FIG. 25.

12. A process for preparation of N-(2-chloropyrimidin-4-yl)-N-2,3-trimethyl-2H-indazol-6-amine Form-K4 characterized by a powder X-Ray diffraction (PXRD) pattern according to FIG. 25, comprising:

a) reacting compound of Formula II with methyl iodide in presence of potassium tert butoxide in dimethylsulfoxide to obtain a compound of Formula III, Formula II

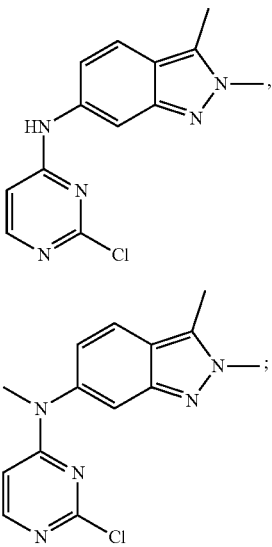

Formula III

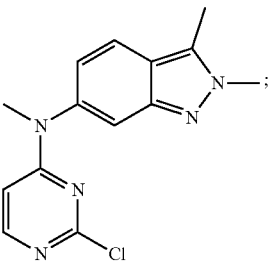

b) concentrating the reaction mass to obtain a residue;

c) adding water to the residue of step b); and d) isolating the Formula III Form-K4.

13. The process of claim 12, wherein the step a) is carried out at a temperature of about 25° C. to about reflux temperature.

14. The process of claim 7, wherein the step b) is carried out by removing the solvent under vacuum at 40° C. to about 45° C.

* * * * *